United States Patent
Chen

(10) Patent No.: US 6,492,520 B1
(45) Date of Patent: Dec. 10, 2002

(54) SUBSTITUTED PYRIDO-OR PYRIMIDO-CONTAINING 6,6- OR 6,7-BICYCLIC DERIVATIVES

(75) Inventor: Yuhpyng L. Chen, Waterford, CT (US)

(73) Assignee: Pfizer Inc, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,076

(22) PCT Filed: Jul. 23, 1997

(86) PCT No.: PCT/IB97/00918

§ 371 (c)(1), (2), (4) Date: May 24, 1999

(87) PCT Pub. No.: WO98/05661

PCT Pub. Date: Feb. 12, 1998

Related U.S. Application Data

(60) Provisional application No. 60/023,453, filed on Aug. 6, 1996.

(51) Int. Cl.[7] .................. C07D 471/04; A61K 31/4375; A61P 25/22
(52) U.S. Cl. ........................ 546/122; 546/123; 514/300
(58) Field of Search ................................ 546/122, 123; 514/300

(56) References Cited

U.S. PATENT DOCUMENTS

| | | | |
|---|---|---|---|
| 4,605,642 A | 8/1986 | River et al. | 514/12 |
| 5,063,245 A | 11/1991 | Abreu et al. | 548/365 |
| 5,457,105 A * | 10/1995 | Barker | 544/284 |

FOREIGN PATENT DOCUMENTS

| | | |
|---|---|---|
| WO | WO 95/197774 | 4/1995 |
| WO | WO9729109 | 8/1997 |
| WO | WO9808846 | 3/1998 |

OTHER PUBLICATIONS

Pulsineli W., (995), The Ischemic Penumbra in Stroke, Scientific American Science & Medicine, pp. 16–25.

Lovenberg T. W., (1995), Corticotropin–Releasing Factor Receptors: Inhibitore, Subtypes, Pharmacology, Localization, and Their Role in Central Nervouse System Function, Current Pharmaceutical Design, pp. 305–316.

Wynn P. C., (1985), Regulation of Corticotripin–Releasing Factor Receptors in the Rat Pituitary Gland: Effects of Adrenalectomy on CRF Receptors and Corticotroph Responses, Endocrinology, vol. 116, pp. 1653–1659.

Grigoriadis D. E. And De Souza E. B., (1989), Corticotropin–Releasing Factor Receptors in Intermediate Lobe of the Pituitary: Biochemical Characterization and Autoradiographic Localization, Peptides, vol. 10, pp. 179–188.

Smith M. A. et al., (1997), Amygdala–Kindled Seizures Increase the Expression of Corticotropin–Releasing Factor (CFR) and CRF–Binding Protein in GABAergic Interneurons of the Dentate Hilus, Brain Research, vol. 745(1,2), pp. 248–255.

Owens, M.J., and Nemeroff, C.B., Pharm. Rev., vol. 43, No. 4 pp. 425–473 (1991).

Fackelmann, K.A., and Raloff, J., Psycholgical Stress Linked to Cancer, Science News, (Sep. 25, 1993) vol. 144, p. 196.

De Souza, *Psychoneuroendocrinology*, vol. 20, No. 8, pp. 789–819 (1995).

Stratakis and Chrousos, *Endocrinology: Basic and Clinical Principles*, Chapter 13, pp. 185–209 (P.M. Conn and S. Melmed, Eds.), Humana Press Inc., Totowa, NJ (1997).

Chalmers, et al., *TiPS*, vol. 17, pp. 166–172 (1996).

* cited by examiner

*Primary Examiner*—Mukund J. Shah
*Assistant Examiner*—Venkataraman Balasubramanian
(74) *Attorney, Agent, or Firm*—Peter C. Richardson; Paul H. Ginsburg; Kristina L. Konstas

(57) ABSTRACT

This invention relates to compounds of formula (I), wherein A, B, D, E, K, G, Z, $R^3$ and $R^5$ are defined as in the specification, and to the pharmaceutically acceptable salts of such compounds. Compounds (I) are corticotropin releasing factor (hormone) CRF (CRH) antagonists.

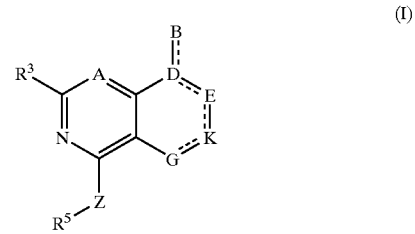

(I)

20 Claims, No Drawings

SUBSTITUTED PYRIDO- OR PYRIMIDO-CONTAINING 6,6- OR 6,7-BICYCLIC DERIVATIVES

This application claims the benefit of U.S. provisional Application No. 60/023,453 filed Aug. 6, 1996.

BACKGROUND OF THE INVENTION

This invention relates to certain pharmaceutically active substituted pyrido- or pyrimido-containing 6,6- or 6,7-bicyclic derivatives, pharmaceutical compositions containing them and methods of administering them to subjects in need of their corticotropin releasing factor antagonist activity.

The substituted heterocyclic derivatives claimed in this case exhibit activity as corticotropin releasing factor (hormone) CRF (CRH) antagonists.

CRF antagonists are mentioned in U.S. Pat. Nos. 4,605,642 and 5,063,245 referring to peptides and pyrazolinones, respectively. They are also referred to in the following: PCT Patent Application PCT/IB95/00439, which designates the United States and was filed on Jun. 6, 1995 and published on Dec. 14, 1995; PCT patent application PCT/IB95/00373, which designates the United States and was filed on May 18, 1995 and published on Dec. 21, 1995; U.S. patent application Ser. No. 08/448,539, which was filed in the PCT on Nov. 12, 1993 and entered the U.S. national phase on Jun. 14, 1995; PCT patent application WO 95/10506, which was filed on Oct. 12, 1993 and published on Apr. 20, 1995, and U.S. patent application 08/481,413, which was filed in the PCT on Nov. 26, 1993 and entered the U.S. national phase on Jul. 24, 1995; U.S. patent application Ser. No. 08/254,820, which was filed on Apr. 19, 1995; Provisional U.S. patent application Ser. No. 60/008,396, which was filed on Dec. 8, 1995; and Provisional U.S. patent application Ser. No. 60/006,333, which was filed on Nov. 8, 1995. All the foregoing patent applications are incorporated herein by reference in their entireties.

The importance of CRF antagonists is set out in the literature, e.g., P. Black, *Scientific American SCIENCE & MEDICINE*, 1995, p. 16–25; T. Lovenberg, et al., *Current Pharmaceutical Design*, 1995, 1, 305–316; and U.S. Pat. No. 5,063,245, which is referred to above. A recent outline of the different activities possessed by CRF antagonists is found in M. J. Owens et al., *Pharm. Rev.*, Vol. 43, pages 425 to 473 (1991), also incorporated herein by reference. Based on the research described in these two and other references, CRF antagonists are effective in the treatment of a wide range of stress-related Illnesses, mood disorders such as depression, major depressive disorder, single episode depression, recurrent depression, child abuse induced depression, postpartum depression, dysthemia, bipolar disorders and cyclothymia; chronic fatigue syndrome; eating disorders such as anorexia and bulimia nervosa; generalized anxiety disorder; panic disorder; phobias; obsessive-compulsive disorder, post-traumatic stress disorder, pain perception such as fibromyalgia; headache; gastrointestinal diseases; hemorrhagic stress; ulcers; stress-induced psychotic episodes; fever; diarrhea; post-operative ileus, colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimers disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiarrhetic hormone; obesity; chemical dependencies and addictions; drug and alcohol withdrawal symptoms; infertility, cancer; infertility; muscular spasms; urinary incontinence; hypoglycemia and immune dysfunctions including stress induced immune dysfunctions, immune suppression and human immunodeficiency virus infections; and stress-induced infections in humans and animals.

The compounds of this invention are also believed to be inhibitors of CRH binding protein and therefore useful in the treatment of disorders the treatment of which can be effected or facilitated by inhibiting such protein. Example of such disorders are Alheimer's disease and obesity.

SUMMARY OF THE INVENTION

The present invention relates to compounds of the formula

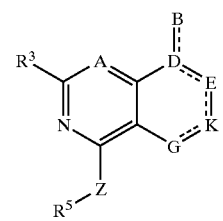

the dashed lines represent optional double bonds;

A is nitrogen or $CR^7$:

B is $-NR^1R^2$, $-CR^1R^2R^{10}$, $-C(=CR^2R^{11})R^1$, $-NHCR^1R^2R^{10}$, $-OCR^1R^2R^{10}$, $-SCR^1R^2R^{10}$, $-CR^2R^{10}NHR^1$, $-CR^2R^{10}OR^1$, $-CR^2R^{10}SR^1$ or $-COR^2$, and is single bonded to D; or B is $-CR^1R^2$, and is double bonded to D and D is carbon;

D is nitrogen or $CR^4$ and is single bonded to all atoms to which it is attached, or D is carbon and is double bonded to E or double bonded to B;

E is oxygen, nitrogen, sulfur, C=O, C=S, $CR^6R^{12}$, $NR^6$ or $CR^6$; or E is a two atom spacer, wherein one of the atoms is oxygen, nitrogen, sulfur, C=O, C=S, $CR^6R^{12}$, $NR^6$ or $CR^6$, and the other is $CR^6R^{12}$ or $CR^9$;

K and G are each, independently, C=O, C=S, sulfur, oxygen, $CHR^8$ or $NR^8$ when single bonded to both adjacent ring atoms, or nitrogen or $CR^8$ when it is double bonded to an adjacent ring atom;

the 6- or 7-membered ring that contains D, E, K and G may contain from one to three double bonds, from zero to two heteroatoms selected from oxygen, nitrogen and sulfur, and from zero to two C=O or C=S groups, wherein the carbon atoms of such groups are part of the ring and the oxygen and sulfur atoms are substituents on the ring;

$R^1$ is $C_1$–$C_6$ alkyl optionally substituted with from one or two substituents independently selected from hydroxy, fluoro, chloro, bromo, iodo, $C_1$–$C_4$ alkoxy, $CF_3$, $-C(=O)(C_1$–$C_4$alkyl), $-C(=O)-O-(C_1$–$C_4)$alkyl, $-OC(=O)(C_1$–$C_4$ alkyl), $-OC(=O)N(C_1$–$C_4$ alkyl)$(C_1$–$C_2$ alkyl), $-NHCO(C_1$–$C_4$ alkyl), $-COOH$, $-COO(C_1$–$C_4$ alkyl), $-CONH(C_1$–$C_4$ alkyl), $-CON(C_1$–$C_4$ alkyl)$(C_1$–$C_2$ alkyl), $-S(C_1$–$C_4$ alkyl), $-CN$, $-NO_2$, —SO($C_1$–$C_4$ alkyl), —$SO_2$($C_4$ alkyl), —$SO_2$NH ($C_1$–$C_4$ alkyl) and —$SO_2$N($C_1$–$C_4$ alkyl)($C_1$–$C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or ($C_1$–$C_4$ alkylene)aryl, wherein said aryl and the aryl moiety of said ($C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl may optionally and independently be replaced by an oxygen or sulfur and wherein each of the foregoing $R^2$ groups may optionally be substituted with from one to three substituents independently selected from chloro, fluoro, hydroxy and $C_1$–$C_4$ alkyl, or with one substituent selected from $C_1$–$C_6$ alkoxy, —OC(=O) ($C_1$–$C_6$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)—CO—($C_1$–$C_4$ alkyl), —NHCO($C_1$–$C_4$ alkyl), —COOH, —COO($C_1$–$C_4$ alkyl), —CONH ($C_1$–$C_4$ alkyl), —CON($C_1$–$C_4$ alkyl)($C_1$–$C_2$ alkyl), —SH, —CN, —$NO_2$, —SO($C_1$–$C_4$ alkyl), —$SO_2$ ($C_1$–$C_4$ alkyl), —$SO_2$NH($C_1$–$C_4$ alkyl) and —$SO_2$N ($C_1$–$C_4$ alkyl)($C_1$–$C_2$ alkyl);

—$NR^1R^2$ or $CR^1R^2R^{10}$ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by $NZ^3$ wherein $Z^3$ is hydrogen or $C_1$–$C_4$ alkyl;

$R^3$ is hydrogen, $C_1$–$C_4$ alkyl, —O($C_1$–$C_4$ alkyl), chloro, fluoro, bromo, iodo, —S($C_1$–$C_4$ alkyl) or —$SO_2$($C_1$–$C_4$ alkyl)

$R^4$ is hydrogen, $C_1$–$C_2$ alkyl, hydroxy or fluoro;

each $R^6$, $R^8$ and $R^9$ that is attached to a carbon atom is selected, independently, from hydrogen, $C_1$–$C_2$ alkyl, fluoro, chloro, bromo, iodo, hydroxy, hydroxymethyl, formyl, trifluoromethyl, cyano, amino, nitro, —O($C_1$–$C_2$ alkyl), —N($C_1$–$C_2$ alkyl)($C_1$–$C_2$ alkyl), —S($C_1$–$C_2$ alkyl), —CO($C_1$–$C_2$ alkyl), —C(=O)H or —C(=O)O($C_1$–$C_2$ alkyl), wherein each of the $C_1$–$C_2$ alkyl moieties in the foregoing $R^6$, $R^8$, and $R^9$ groups may optionally contain one double or triple bond; and each $R^6$, $R^8$, and $R^9$ that is attached to a nitrogen atom is selected, independently, from hydrogen and $C_1$–$C_4$ alkyl;

$R^5$ is substituted phenyl, naphthyl, pyridyl or pyrimidyl, wherein each of the foregoing $R^5$ groups is substituted with from two to four substituents $R^{15}$, wherein from one to three of said substituents may be selected, independently, from chloro, $C_1$–$C_6$ alkyl, —O($C_1$–$C_6$ alkyl) and —($C_1$–$C_6$ alkylene)O($C_1$–$C_6$ alkyl), and wherein one of said substituents may be selected, independently, from bromo, iodo, formyl, cyano, trifluoromethyl, nitro, amino, —NH($C_1$–$C_4$ alkyl), —N($C_1$–$C_2$ alkyl)($C_1$–$C_5$ alkyl), —C(=O)O($C_1$–$C_4$ alkyl), —C(=O)($C_1$–$C_4$ alkyl), —COOH, —$SO_2$NH ($C_1$–$C_4$ alkyl), —$SO_2$N($C_1$–$C_2$ alkyl)($C_1$–$C_4$ alkyl), —$SO_2NH_2$, —$NHSO_2$($C_1$–$C_4$ alkyl), —S($C_1$–$C_6$ alkyl) and —$SO_2$($C_1$–$C_6$ alkyl), and wherein each of the $C_1$–$C_4$ alkyl and $C_1$–$C_6$ alkyl moieties in the foregoing $R^5$ groups may optionally be substituted with one or two substituents independently selected from fluoro, hydroxy, amino, methylamino, dimethylamino and acetyl;

$R^7$ is hydrogen, methyl, halo (e.g., chloro, fluoro, Iodo or bromo), hydroxy, methoxy, —C(=O)($C_1$–$C_2$ alkyl), —C(=O)O($C_1$–$C_2$ alkyl), trifluoromethoxy, hydroxymethyl, trifluoromethyl, or formyl;

$R^{10}$ is hydrogen, hydroxy, methoxy or fluoro;

$R^{11}$ is hydrogen or $C_1$–$C_4$ alkyl;

$R^{12}$ is hydrogen or methyl; and

Z is NH, oxygen, sulfur, —N($C_1$–$C_4$ alkyl), or $CR^{13}R^{14}$ wherein $R^{13}$ and $R^{14}$ are independently selected from hydrogen, and methyl with the exception that one of $R^{13}$ and $R^{14}$ may optionally be cyano;

with the proviso that: (a) in the six or seven membered rings of structures in formula I, there can not be two double bonds adjacent to each other; and (b) when D is carbon and is double bonded to B, then B is $CR^1R^2$;

and the pharmaceutically acceptable salts of such compounds.

Examples of more specific embodiments of formula I are the following, wherein (R)n represents from zero to two substituents, wherein such substitutents are as defined above in the definition of formula 1.

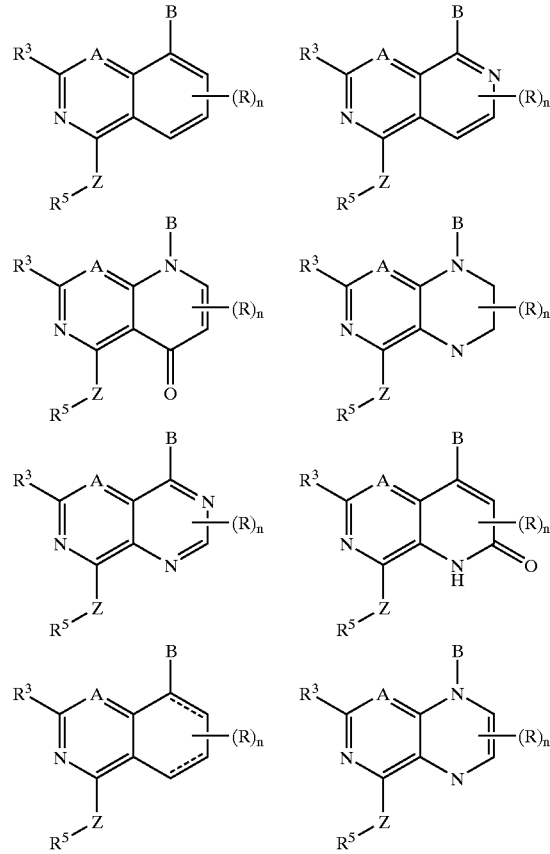

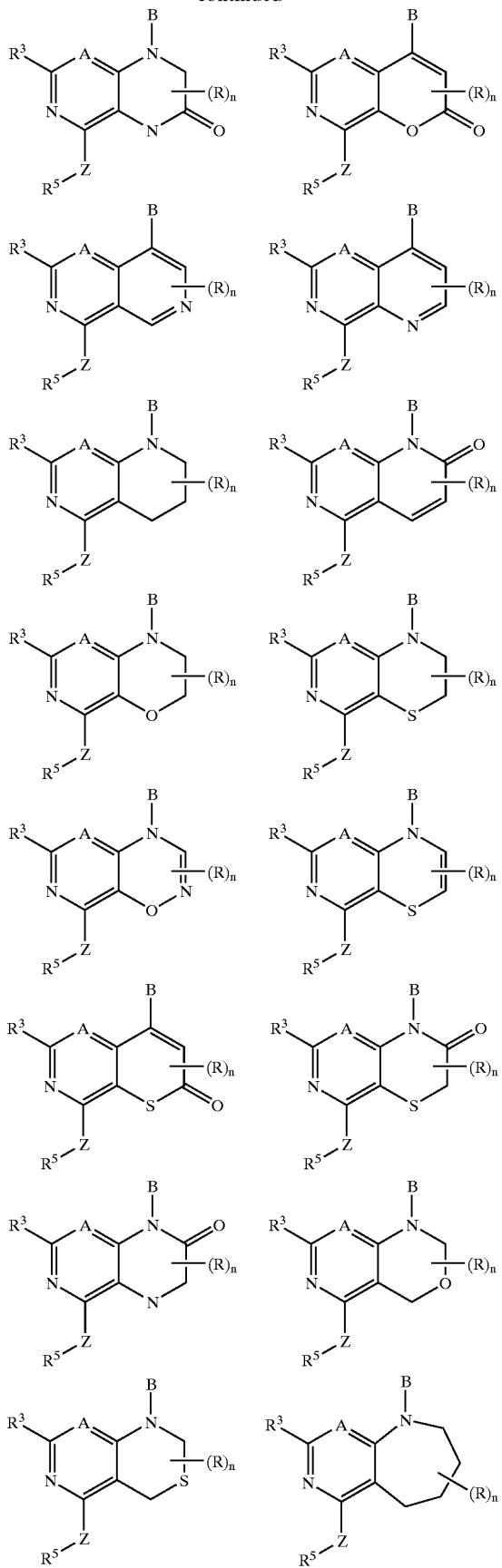
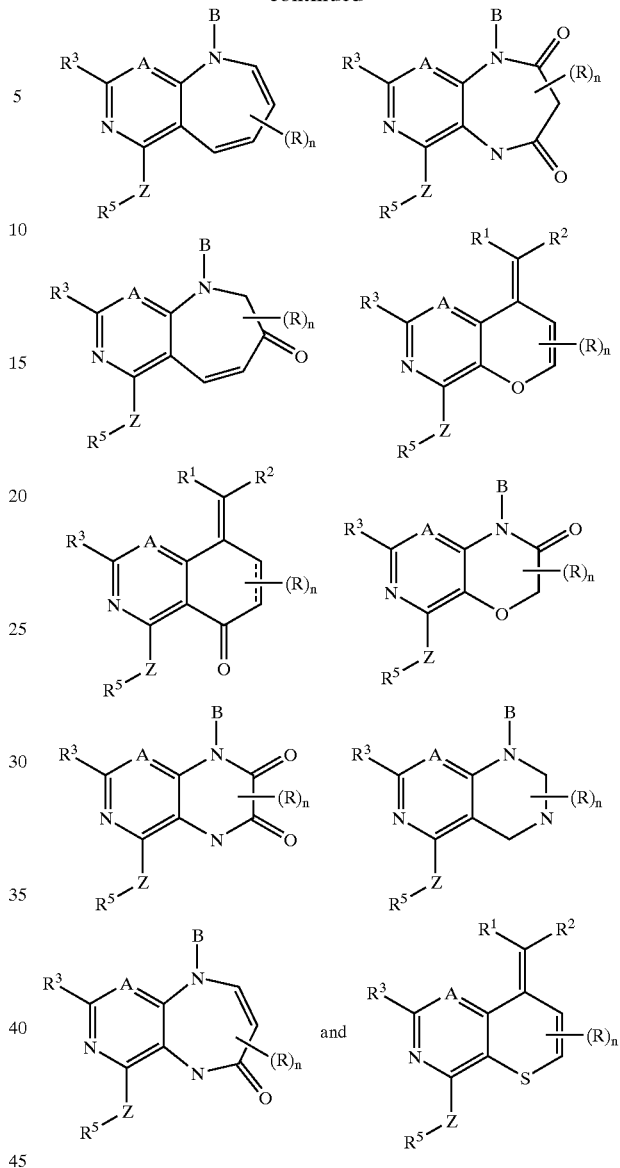

More specific embodiments of this invention include compounds of the formula I wherein B is —CHR$^1$R$^2$ or —NR$^1$R$^2$, and R$^1$ is C$_1$–C$_6$ alkyl which may optionally be substituted with one hydroxy, fluoro, trifluoromethyl or C$_1$–C$_4$ alkoxy group and may optionally contain one double or triple bond; and R$^2$ is benzyl or C$_1$–C$_6$ alkyl which may optionally contain one double or triple bond, and wherein said C$_1$–C$_6$ alkyl and the phenyl moiety of said benzyl may optionally be substituted with one fluoro, C$_1$–C$_2$ alkyl, C$_1$–C$_2$ alkoxy or chloro group.

Other more specific embodiments of the invention include compounds of formula I wherein R$^3$ is methyl, ethyl, chloro or methoxy; R$^6$, R$^8$ and R$^9$ are selected, independently, from hydrogen and methyl; R$^5$ is di- or tri-substituted phenyl, pyridyl, or pyrimidyl, in which up to three of the substitutents can be independently selected from C–C$_4$ alkyl, —O—(C$_1$–C$_4$ alkyl) and (C$_1$–C$_2$ alkylene)—O—(C$_1$–C$_4$ alkyl), and wherein one of the substituents can be independently selected from trifluoromethyl, trifluoromethoxy, —CHO, (C$_1$–C$_4$ alkyl)—OH, cyano, chloro, fluoro, bromo, iodo and nitro, and wherein each of the foregoing (C$_1$–C$_4$) alkyl groups may optionally contain one double or triple bond; and Z is oxygen or NH.

Other more specific embodiments of the invention include compounds of the formula I wherein A is nitrogen or CH. Examples of preferred compounds of the invention are:

1-(1-ethyl-propyl)-4,7-dimethyl-5-(2,4,6-trimethyl-phenoxy)-1,4-dihydro-2H-pyrido[3,4-b]pyrazin-3-one;

1-(1-ethyl-propyl)-4,7-dimethyl-5-(2,4,6-trimethyl-phenoxy)-1,4-dihydro-2H-pyrido[3,4-b]pyrazin-3-one;

1-(1-ethyl-propyl)-4,7-dimethyl-5-(2,4,6-trimethyl-phenoxy)-1,2,3,4-tetrahydro-pyrido[3,4-b]pyrazine;

1-(1-ethyl-propyl)-7-methyl-5-(2,4,6-trimethyl-phenoxy)-1,2,3,4-tetrahydro-pyrido[3,4-b]pyrazine;

1-(1-ethyl-propyl)-7-methyl-2-oxo-5-(2,4,6trimethyl-phenoxy)-1,2,3,4-tetrahydro-[1,6]naphthyridine-3-carboxylic acid methyl ester;

1-(1-ethyl-propyl)-7-methyl-2-oxo-5-(2,4,6-trimethyl-phenoxy)-1,2,3,4-tetrahydro-[1,6]naphthyridine-3-carboxylic acid isopropyl ester;

1-(1-ethyl-propyl)-7-methyl-5-(2,4,6-trimethyl-phenoxy)-3,4-dihydro-1H-[1,6]naphthyridin-2-one;

1-(1-ethyl-propyl)-7-methyl-5-(2,4,6-trimethyl-phenoxy)-1,2,3,4-tetrahydro-[1,6]naphthyridine;

1-(1-ethyl-propyl)-7-methyl-5-(2,4,6-trimethyl-phenoxy)-1,4-dihydro-2H-3-oxa-1,6-diaza-naphthalene;

1-(1-ethyl-propyl)-4,7-dimethyl-5-(2,4,6-trimethyl-phenoxy)-1,4-dihydro-2H-3-oxa-1,6-diaza-naphthalene;

1-(1-ethyl-propyl)-3,7-dimethyl-5-(2,4,6-trimethyl-phenoxy)-3,4-dihydro-1H-3-oxa-[1,6]-naphthyridin-2-one; and 1-(1-ethyl-propyl)-3,3,6-trimethyl-4-(2,4,6-trimethyl-phenoxy)-2,3-dihydro-1H-pyrrolo[3,2-c]pyridine.

Other compounds of the formula I include the following:

1-(1-ethyl-propyl)-4,7-dimethyl-5-(4-bromo-2,6-dimethyl-phenoxy)-1,4-dihydro-2H-pyrido[3,4-b]pyrazin-3-one;

1-(1-ethyl-propyl)-4,7-dimethyl-5-(4-bromo-2,6-dimethyl-phenoxy)-1,4-dihydro-2H-pyrido[3,4-b]pyrazin-3-one;

1-(1-ethyl-propyl)-4,7-dimethyl-5-(4-bromo-2,6-dimethyl-phenoxy)-1,2,3,4-tetrahydro-pyrido[3,4-b]pyrazine;

1-(1-ethyl-propyl)-7-methyl-5-(4-bromo-2,6-dimethyl-phenoxy)-1,2,3,4-tetrahydro-pyrido [3,4-b]pyrazine;

1-(1-ethyl-propyl)-7-methyl-2-oxo-5-(4-bromo-2,6-dimethyl-phenoxy)-1,2,3,4-tetrahydro-[1,6]naphthyridine-3-carboxylic acid methyl ester;

1-(1-ethyl-propyl)-7-methyl-2-oxo-5-(4-bromo-2,6-dimethyl-phenoxy)-1,2,3,4-tetrahydro-[1,6]naphthyridine-3-carboxylic acid isopropyl ester;

1-(1-ethyl-propyl)-7-methyl-5-(4-bromo-2,6-dimethyl-phenoxy)-3,4-dihydro-1H-[1,6]naphthyridin-2-one;

1-(1-ethyl-propyl)-7-methyl-5-(4-bromo-2,6-dimethyl-phenoxy)-1,2,3,4-tetrahydro-[1,6]naphthyridine;

1-(1-ethyl-propyl)-7-methyl-5-(4-bromo-2,6-dimethyl-phenoxy)-1,4-dihydro-2H-3-oxa-1,6diaza-naphthalene;

1-(1-ethyl-propyl)-4,7-dimethyl-5-(4-bromo-2,6-dimethyl-phenoxy)-1,4-dihydro-2H-3-oxa-1,6-diaza-naphthalene;

1-(1-ethyl-propyl)-3,7-dimethyl-5-(4-bromo-2,6-dimethyl-phenoxy)-3,4-dihydro-1H-3-oxa-[1,6]-naphthyridin-2-one;

1-(1-ethyl-propyl)-3,3,6-trimethyl-4-(4-bromo-2,6-dimethyl-phenoxy)-2,3-dihydro-1H-pyrrolo[3,2-c]pyridine;

1-(1-ethyl-propyl)-4,7-dimethyl-5-(4-chloro-2,6-dimethyl-phenoxy)-1,4-dihydro-2H-pyrido [3,4-b] pyrazin-3-one;

1-(1-ethyl-propyl)-4,7-dimethyl-5-(4-chloro-2,6-dimethyl-phenoxy)-1,4-dihydro-2H-pyrido[3,4-b]pyrazin-3-one;

1-(1-ethyl-propyl)-4,7-dimethyl-5-(4-chloro-2,6-dimethyl-phenoxy)-1,2,3,4-tetrahydro-pyrido[3,4-b]pyrazine;

1-(1-ethyl-propyl)-7-methyl-5-(4-chloro-2,6-dimethyl-phenoxy)-1,2,3,4-tetrahydro-pyrido[3,4-b]pyrazine;

1-(1-ethyl-propyl)-7-methyl-2-oxo-5-(4-chloro-2,6-dimethyl-phenoxy)-1,2,3,4-tetrahydro-[1,6]naphthyridine-3-carboxylic acid methyl ester;

1-(1-ethyl-propyl)-7-methyl-2-oxo-5-(4-chloro-2,6-dimethyl-phenoxy)-1,2,3,4-tetrahydro-[1,6]naphthyridine-3-carboxylic acid isopropyl ester;

1-(1-ethyl-propyl)-7-methyl-5-(4-chloro-2,6-dimethyl-phenoxy)-3,4-dihydro-1H-[1,6]naphthyridin-2-one;

1-(1-ethyl-propyl)-7-methyl-5-(4-chloro-2,6-dimethyl-phenoxy)-1,2,3,4-.tetrahydro[1,6]naphthyridine;

1-(1-ethyl-propyl)-7-methyl-5-(4-chloro-2,6-dimethyl-phenoxy)-1,4-dihydro-2H-3-oxa-1,6-diaza-naphthalene;

1-(1-ethyl-propyl)-4,7-dimethyl-5-(4-chloro-2,6-dimethyl-phenoxy)-1,4-dihydro-2H-3-oxa-1,6-diaza-naphthalene;

1-(1-ethyl-propyl)-3,7-dimethyl-5-(4-chloro-2,6-dimethyl-phenoxy)-3,4-dihydro-1H-3-oxa-[1,6-naphthyridin-2-one;

1-(1-ethyl-propyl)-3,3,6-trimethyl-4-(4-chloro-2,6-dimethyl-phenoxy)-2,3-dihydro-1H-pyrrolo[3,2-c]pyridine;

1-(1-ethyl-propyl)-7-methyl-5-(2,4,6-trimethyl-phenoxy)-1,4-dihydro-2H-pyrimido[4,5-d][1,3]oxazine;

[1-(1-ethyl-propyl)-7-methyl-1,4-dihydro-2H-3-oxa-1,6-diaza-naphthalen-5-yl]-(2,4,6-trimethyl-phenyl)-amine;

[1-(1-ethyl-propyl)-7-methyl-1,4-dihydro-2H-pyrimido[4,5-d][1,3]oxazin-5-y-(2,4,6-trimethyl-phenyl)-amine;

3-[7-methyl-5-(2,4,6-trimethyl-phenoxy)-4H-3-oxa-1,6-diaza-naphthalen-1-yl]-pentan-1-ol; 2-[7-methyl-5-(2,4,6-trimethyl-phenoxy)-4H-3-oxa-1,6-diaza-naphthalen-1-yl]-butan-1-ol;

1-(1-ethyl-butyl)-7-methyl-5-(2,4,6-trimethyl-phenoxy)-1,4-dihydro-2H-3-oxa-1,6-diaza-naphthalene;

7-methyl-1-(1-propyl-butyl)-5-(2,4,6-trimethyl-phenoxy)-1,4-dihydro-2H-3-oxa-1,6-diaza-naphthalene;

1-(1-ethyl-propyl)-7-methyl-5-(2,4,6-trimethyl-phenylamino)-1,4-dihydro-2H-pyrido[3,4-b]pyrazin-3-one;

8-(1-ethyl-propyl)-2-methyl4-(2,4,6-trimethyl-phenylamino)-7,8-dihydro-5H-pyridin-6-one;

8-(1-ethyl-propyl)-2-methyl-4-(2,4,6trimethyl-phenoxy)-7,8-dihydro-5H-pyridin-6-one;

8-(1-ethyl-propyl)-2-methyl-4-(2,4,6-trimethyl-phenoxy)-5,6,7,8-tetrahydro-pyridine;

[8-(1-ethyl-propyl)-2-methyl-5,6,7,8-tetrahydro-pyridin-4-yl]-(2,4,6-trimethyl-phenyl)-amine;

[1-(1-ethyl-propyl)-7-methyl-1,2,3,4-tetrahydro-pyrido[3,4-b]pyrazin-5-yl]-(2,4,6-trimethyl-phenyl)-amine;

[1-(1-ethyl-propyl)-7-methyl-1,2,3,4-tetrahydro-pyrido[3,4-b]pyrazin-5-yl]-(2,4,6-trimethyl-phenyl)-amine;

1-(1-ethyl-propyl)-7-methyl-5-(2,4,6-trimethyl-phenoxy)-1,2,3,4-tetrahydro-pyrido[3,4-b]pyrazine;

8-(1-ethyl-propyl)-2-methyl-4-(2,4,6-trimethyl-phenoxy)-5,6,7,8-tetrahydro-pyridine;

[8-(1-ethyl-propyl)-2-methyl-5,6,7,8-tetrahydro-pyridin-4-yl]-(2,4,6-trimethyl-phenyl)-amine;

[1-(1-ethyl-propyl)-7-methyl-1,2,3,4-tetrahydro-[1,6]naphthyridin in-5-yl]-(2,4,6-trimethyl-phenyl)-amine;

8-(1-ethyl-propyl)-2-methyl-4-(2,4,6-trimethyl-phenoxy)-5,6,7,8-tetrahydro-pyrido(2,3d]pyrimidine;

[8-(1-ethyl-propyl)-2-methyl-5,6,7,8-tetrahydro-pyrido[2,3-d]pyrimidin-4yl]-(2,4,6-trimethyl-phenyl)-amine;

1-(1-ethyl-propyl)-4,7-dimethyl-5-(2,4,6-trimethyl-phenoxy)-1,4-dihydro-2H-pyrimido[4,5-d][1,3]oxazine;

[1-(1-ethyl-propyl)-4,7-dimethyl-1,4-dihydro-2H-pyrimido[4,5-d][1,3]oxazin-5-yl]-(2,4,6-trimethyl-phenyl)-amine;

[1-(1-ethyl-propyl)-4,7-dimethyl-1,4-dihydro-2H-3-oxa-1,6-diaza-naphthalen-5-yl]-(2,4,6-trimethyl-phenyl)-amine;

1-(1-hydroxymethyl-propyl)-7-methyl-5-(2,4,6-trimethyl-phenoxy)-1,4-dihydro-2H-pyrido[3,4-b]pyrazin-3-one;

1-(1-hydroxymethyl-propyl)-4,7-dimethyl-5-(2,4,6-trimethyl-phenoxy)-1,4-dihydro-2H-pyrido[3,4-b]pyrazin-3-one;

2-[4,7-dimethyl-5-(2,4,6-trimethyl-phenoxy)-3,4-dihydro-2H-pyrido[3,4-b]pyrazin-1-yl]-butan-1-ol;

2-[7-methyl-5-(2,4,6-trimethyl-phenoxy)-3,4-dihydro-2H-pyrido[3,4-b]pyrazin-1-yl]-butan-1-ol;

2-[7-methyl-5-(2,4,6-trimethyl-phenoxy)-3,4-dihydro-2H-[1,6]naphthyridin-1-yl]-butan-1-ol;

2-[4,7-dimethyl-5-(2,4,6-trimethyl-phenoxy)4H-3-oxa-1,6-diaza-naphthalen-1-yl]-butan-1-ol;

5-(1-ethyl-propyl)-3-methyl-1-(2,4,6-trimethyl-phenoxy)-isoquinoline;

diethyl-[3-methyl-1-(2,4,6-trimethyl-phenoxy)-isoquinolin-5-yl]-amine;

[5-(1-ethyl-propyl)-3-methyl-isoquinolin-1-yl]-(2,4,6-trimethyl-phenyl)-amine;

N-5-butyl-N-5-ethyl-3-methyl-N1-(2,4,6-trimethyl-phenyl)-isoquinoline-1,5-diamine;

5-(1-ethyl-propyl)-3-methyl-1-(2,4,6-trimethyl-phenoxy)-[2,6]naphthyridine;

5(1-ethyl-propyl)-3-methyl-1-(2,4,6-tnimethyl-phenoxy)-[2,7]naphthyridine;

4-(1-ethyl-propyl)-6-methyl-8-(2,4,6-trimethyl-phenoxy)-[1,7]naphthyridine;

[5-(1-ethyl-propyl)-3-methyl-[2,6]naphthyridin-1-yl]-(2,4,6-trimethyl-phenyl)-amine;

1-(1-ethyl-propyl)-7-methyl-5-(2,4,6-trimethyl-phenylamino-1H-[1,6]naphthyridin-2-one;

4-(1-ethyl-propyl)-6-methyl-8-(2,4,6-trimethyl-phenoxy)-1H-[1,7]naphthyridin-2-one;

4-diethylamino-6-methyl-8-(2,4,6-trimethyl-phenoxy)-1H-[1,7]naphthyridin-2-one;

4-diethylamino-6-methyl-8-(2,4,6-trimethyl-phenoxy)-1H-[1,7]naphthyridin-2-one;

1-(1-ethyl-propyl)-7-methyl-5-(2,4,6-trimethyl-phenoxy)-1,2,3,4-tetrahydro-pyrido[3,4-b]pyrazine;

1-(1-ethyl-propyl)-7-methyl-5-(2,4,6-trimethyl-phenoxy)-2,3-dihydro-1H-4-oxa-1,6-diaza-naphthalene;

1-(1-ethyl-propyl)-7-methyl-5-(2,4,6-trimethyl-phenoxy)-2,3-dihydro-1H-4-thia-1,6-diaza-naphthalene;

[1-(1-ethyl-propyl)-7-methyl-1,2,3,4-tetrahydro-[1,6]naphthyridin-5-yl]-(2,4,6-trimethyl-phenyl)-amine;

[1-(1-ethyl-propyl)-7-methyl-2,3-dihydro-1H-4-oxa-1,6-diaza-naphthalen-5-yl]-(2,4,6-trimethyl-phenyl)-amine;

[1-(1-ethyl-propyl)-7-methyl-2,3-dihydro-1H4-thia-1,6-diaza-naphthalen-5-yl]-(2,4,6-trimethyl-phenyl)-amine;

[1-(1-ethyl-propyl)-7-methyl-1,2,3,4-tetrahydro-pyrido[3,4-b]pyrazin-5-yl]-(2,4,6-trimethyl-phenyl)-amine;

[1-(1-ethyl-propyl)-7-methyl-1,2,3,4-tetrahydro-pyrido[3,4-b]pyrazin-5-yl]-(2,4,6-trimethyl-phenyl)-amine;

1-(1-ethyl-propyl)-7-methyl-5-(2,4,6-trimethyl-phenoxy)-1,4-dihydro-2H-3-thia-1,6-diaza-naphthalene;

1-(1-ethyl-propyl)-7-methyl-5-(2,4,6-trimethyl-phenoxy)-1,2,3,4-tetrahydro-pyrido[4,3-d]pyrimidine;

1-(1-ethyl-propyl)-3,7-dimethyl-5-(2,4,6-trimethyl-phenoxy)-1,2,3,4-tetrahydro-pyrido[4,3-d]pyrimidine;

1-(1-ethyl-propyl)-4,7-dimethyl-5-(2,4,6-trimethyl-phenoxy)-1,2,3,4-tetrahydro-[1,6]naphthyridine tetrahydro-pyrido[4,3-d]pyrimidine;

1-(1-ethyl-propyl)-4,7-dimethyl-5-(2,4,6-trimethyl-phenoxy)-1,4-dihydro-2H-3-thia-1,6-diaza-naphthalene;

1-(1-ethyl-propyl)-4,7-dimethyl-5-(2,4,6-trimethyl-phenoxy)-1,2,3,4-tetrahydro-pyrido[4,3-d]pyrimidine;

4-(1-ethyl-propyl)-6-methyl-8-(2,4-trimethyl-phenoxy)-pyrano[2,3-c]pyridin-2-one;

1-sec-butyl-7-methyl-5-(2,4,6-trimethyl-phenoxy)-1,4-dihydro-2H-pyrido[3,4-b]pyrazin-3-one;

1-sec-butyl-7-methyl-5-(2,4,6-trimethyl-phenoxy)-1,2,3,4-tetrahydro-[1,6]3naphthyridine;

1-sec-butyl-7-methyl-5-(2,4,6-trimethyl-phenoxy)-1,4-dihydro-2H-3-oxa-1,6-diaza-naphthalene;

1-sec-butyl-7-methyl-5-(2,4,6-trimethyl-phenoxy)-1,2,3,4-tetrahydro-pyrido[3,4-b]pyrazine;

1-sec-butyl-4,7-dimethyl-5-(2,4,6-trimethyl-phenoxy)-1,4dihydro-2H-3-ixa-1,6-diaza-napthalene;

1-sec-butyl4,7-dimethyl-5-(2,4,6-trimethyl-phenoxy)-1,2,3,4-tetrahydro-pyrido[3,4-]pyrazine;

7-methyl-1-(1-propyl-butyl)-5-(2,4,6-trimethyl-phenoxy)-1,2,3,4-tetrahydro-[1,6]naphthyridine;

5-sec-butyl-3-methyl-1-(2,4,6trimethyi-phenoxy)-isoquinoline;

diethyl-[3-methyl-1-(2,4,6-trimethyl-phenoxy)-isoquinolin-5-yl]-amine;

[5-sec-butyl-3-methyl-isoquinolin-1-yl]-(2,4,6-trimethyl-phenyl)-amine;

N-5-butyl-N-ethyl-3methyl-N1-(2,4,6-trimethyl-phenyl)-isoquinoline-1,5diamine;

5-sec-butyl-3-methyl-1-(2,4,6-trimethyl-phenoxy)-[2,61naphthyeidine;

5-sec-butyl-3-methyl-1-(2,4,6-trimethyl-phenoxy)-[2,7]naphthyridine;

4-sec-butyl-6-methyl-8-(2,4,6-trimethyl-phenoxy)-[1,7]naphthyridine;

[5-sec-butyl-3-methyl-[2,6]naphthyridin-1-yl]-(2,4,6trimethyl-phenyl)-amine;

1-sec-butyl-7-methyl-5-(2,4,6tnimethyl-phenylamino)-1H-[1,6]naphthyridin-2-one;

4-sec-butyl-6-methyl-8-(2,4,6-trimethyl-phenoxy)-1H-[1,7]naphthyridin-2-one;

4-diethylamino-6-methyl-8-(2,4,6-trimethyl-phenoxy)-1H-[1,7]naphthyridin-2-one;

4-diethylamino-6-methyl-8-(2,4,6-trimethyl-phenoxy)-1H-[1,7]naphthyridin-2-one;

1-sec-butyl-7-methyl-5-(2,4,6-trimethyl-phenoxy)-1,2,3,4-tetrahydro-pyrido[3,4-b]pyrazine;

1-sec-butyl-7-methyl-5-(2,4,6-trimethyl-phenoxy)-2,3-dihydro-1H-4-oxa-1,6-diaza-naphthalene;

1-sec-butyl-7-methyl-5-(2,4,6-trimethyl-phenoxy)-2,3-dihydro-1H-4-thia-1,6-diaza-naphthalene;

[1-sec-butyl-7-methyl-1,2,3,4-tetrahydro-[1,6]naphthyridin-5-yl]-(2,4,6-trimethyl-phenyl)-amine;

[1-sec-butyl-7-methyl-2,3-dihydro-1H-4-oxa-1,6-diaza-naphthalen-5-yl]-(2,4,6trimethyl-phenyl)-amine;

[1-sec-butyl-7-methyl-2,3-dihydro-1H-4-thia-1,6-diaza-naphthalen-5-yl]-(2,4,6-trimethyl-phenyl)-amine;

[1-sec-butyl-7-methyl-1,2,3,4-tetrahydro-pyrido [3,4-b]pyrazin-5-yl]-(2,4,6-trimethyl-phenyl)-amine;

[1-sec-butyl-7-methyl-1,2,3,4-tetrahydro-pyrido[3,4-b]pyrazin-5-yl]-(2,4,6-trimethyl-phenyl)-amine;

1-sec-butyl-7-methyl-5-(2,4,6-trimethyl-phenoxy)-1,4-dihydro-2H-3-thia-1,6-diaza-naphthalene;

1-sec-butyl-7-methyl-5-(2,4,6-trimethyl-phenoxy)-1,2,3,4-tetrahydro-pyrido-[4,3-d]pyrimidine;

1-sec-butyl-3,7-dimethyl-5-(2,4,6-trimethyl-phenoxy)-1,2,3,4-tetrahydro-pyrido-[4,-d]pyrimidine;

1-sec-butyl-4,7-dimethyl-5-(2,4,6-trimethyl-phenoxy)-1,2,3,4-tetrahydro-[1,6]-naphthyridine tetrahydro-pyrido[4,3-d]pyrimidine;

1-sec-butyl-4,7-dimethyl-5-(2,4,6-trimethyl-phenoxy)-1,4-dihydro-2H-3-thia-1,6-diaza-naphthalene;

1-sec-butyl-4,7-dimethyl-5-(2,4,6-trimethyl-phenoxy)-1,2,3,4tetrahydro-pyrido-[4,3-d]pyrimidine; and 4-sec-butyl-6-methyl-8-(2,4,6-trimethyl-phenoxy)-pyrano[2,3-c]pyridin-2-one.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

The invention also relates to a pharmaceutical composition for the treatment, prevention or inhibition of (a) a disorder the treatment of which can be effected or facilitated by antagonizing CRF, including but not limited to disorders induced or facilitated by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia;

mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus (HIV) infections; neurodegenerative diseases such as Alzheimers disease, Parkinson's disease and Huntington's disease; gastrointestinal diseases; eating disorders such as anorexia and bulimia nervosa; hemorrhagic stress; chemical dependencies and addictions (e.g., dependencies on alcohol, nicotine, cocaine, heroin, benzodiazepines, or other drugs); drug and alcohol withdrawal symptoms; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; hypertension; tachycardia; congestive heart failure; osteoporosis; premature birth; and hypoglycemia in a mammal, including a human, comprising an amount of a compound of the formula I or a pharmaceutically acceptable salt thereof, that is effective in the treatment of such disorder, and a pharmaceutically acceptable carrier.

The invention also relates to a method for the treatment, prevention or inhibition of (a) a disorder the treatment of which can be effected or facilitated by antagonizing CRF, including but not limited to disorders induced or facilitator by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome; Crohn's disease; spastic colon; post operative ileus; ulcer; diarrhea; stress-induced fever; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimers type; multiinfarct dementia; amyotrophic lateral sclerosis; chemical dependencies and addictions (e.g., dependencies on alcohol, nicotine, cocaine, heroin, benzodiazepines, or other drugs); drug and alcohol withdrawal symptoms; hypertension; tachycardia; congestive heart failure; osteoporosis; premature birth; and hypoglycemia in a mammal, including a human, comprising administering to a subject in need of said treatment an amount of a compound of the formula I, or a pharmaceutically acceptable salt thereof, that is effective in treating such disorder.

This invention also relates to a method of treating or preventing a disorder or condition, the treatment or prevention of which can be effected or facilitated by inhibiting CRH binding protein in a mammal, including a human, comprising administering to said mammal a CRH binding protein inhibiting amount of a compound of the formula I or a pharmaceutically acceptable salt thereof.

This invention also relates to a pharmaceutical composition for treating or preventing a disorder or condition, the treatment or prevention of which can be effected or facilitated by inhibiting CRH binding protein in a mammal, including a human, comprising a CRH binding protein inhibiting amount of a compound of the formula I, or a pharmaceutically acceptable salt thereof, and a pharmaceutically acceptable carrier.

The invention further includes intermediate compounds of formulas

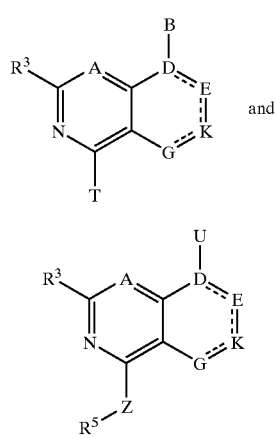

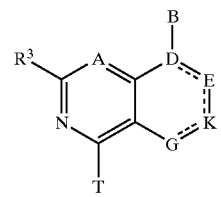

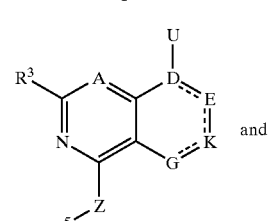

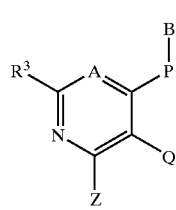

a wherein T is chloro, bromo, iodo, or —OSO$_2$CF$_3$; U is CN, —COO(C$_1$–C$_4$ alkyl), chloro, bromo, iodo, —OSO$_2$CF$_3$, hydroxy or amino when D is carbon, and U is hydrogen when D is nitrogen.

This invention includes all optical isomers and other stereoisomers of compounds of the formula I. When such compounds contain one or more chiral centers, it is understood that the invention includes the racemic mixtures as well as all individual enantiomers and diastereomers of such compounds, and mixtures thereof.

The compounds of this invention include compounds identical to those described above but for the fact that one or more hydrogen, nitrogen or carbon atoms are replaced by isotopes thereof (e.g., tritium or carbon-14 isotopes). Such compounds are useful as research and diagnostic tools in metabolism pharmokinetic studies and in binding assays.

DETAILED DESCRIPTION OF THE INVENTION

The following compounds having the formulas II, III, and IV are useful as intermediates in the synthesis of compounds of the formula I.

In the above compounds of formulas II to IV, M is chloro, bromo, iodo, —OSO$_2$CF$_3$ or ZR$^5$; P is NH, CHCN or CHCOO(C$_1$–C$_4$ alkyl); Q is amino, —(C$_1$–C$_2$ alkyl)CH [COO(C$_1$–c$_4$alkyl)]$_2$, (C$_2$–C$_3$ alkyl)-CN, hydroxy or mercapto, and A, B, D, E, K and G are defined as above.

Methods of preparing the compounds and compositions of this invention are described below. In the discussion and reaction schemes that follow, R$^1$ through R$^{14}$, R$^{12}$, A, B, D, E, K, G, Z, T, M, P, Q, and U, the dashed lines and structural formulas I, II, III, and IV, unless otherwise indicated, are defined as above.

SCHEME 1

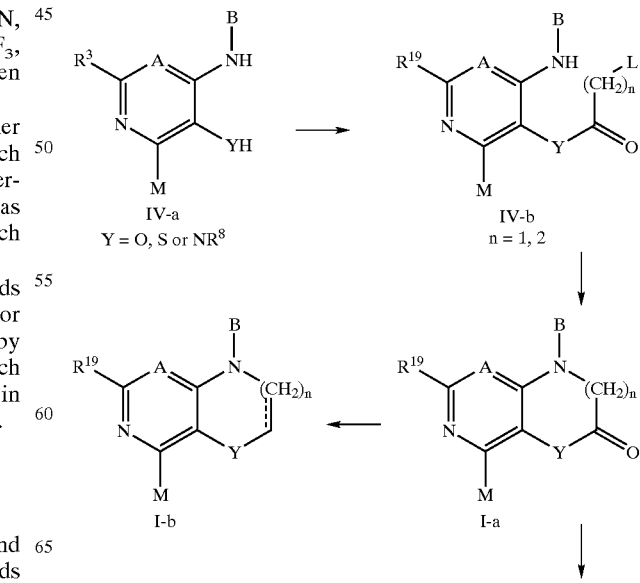

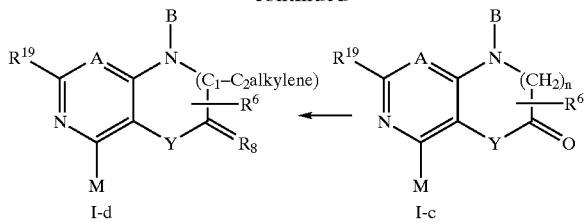

SCHEME 2

Compounds of the formula I may be prepared by reacting a compound of the formula 11 with the corresponding compound of the formula $R^5ZH$. This reaction is generally carried out with or without a solvent, in the presence of a base, at a temperature from about 0° C. to about 270° C., at a pressure from about 14 psi to about 300 psi. Suitable solvents include organic solvents such as tetrahydrofuran (THF), acetonitrile, N,N-dimethylformamide (DMF), dimethylsulfoxide (DMS0), acetone, $C_2$–$C_{15}$ alcohols, chloroform, dioxane, chlorobenzene, benzene, toluene, xylene, sulfolane, pyridine, quinoline, 2,4,6-trimethylpyridine, acetamide, di-($C_1$–$C_2$)alkylacetamide, and 1-methyl-2-pyrrolidinone (NMP).

When Z is NH, an excess of $R^5ZH$, may be used both as the reagent and as the base. Examples of bases other than $R^5ZH$ that may be used include potassium carbonate, sodium hydride, potassium hydride, sodium ($C_1$–$C_4$) alkoxides, potassium ($C_1$–$C_4$) alkoxides, sodium, sodium amide, tri-[($C_1$–$C_4$) alkyllamines, organolithium or organosodium compounds such as n-butyllithium, s-butyllithium, t-butyllithium, lithium diisopropylimide, lithium bis (trimethylsilyl)amide, sodium diisopropylamide or sodium bis(trimethylsilyl)amide, and organometallic bases such as Grignard reagents. This reaction is generally carried out in an appropriate solvent (e.g., THF, dioxane, sulfolane, DMSO, toluene, DMF or NMP, with or without an additional catalyst such as a copper halide, oxide or sulfate e.g., CuI, CuBr, $Cu_2O$, CuCl, $CuSO_4$ $Cu_2$. $CuBr_2$, $CuCl_2$ or Cu(O)), a Pd(O) salt such as $Pd(PPH_3)_4$, a Pd(II) salt such as $Pd(OAc)_2$ (wherein OAc is acetate) with racemic or (R)— or (S)-2,2-bis(diphenylphosphino)-1,1-binaphthyl (BINAP), at temperature from about room temperature to about 270° C.

When Z is oxygen or sulfur, a base that is capable of deprotonating $R^5ZH$ may be used, such as potassium carbonate, sodium carbonate, sodium, sodium amide, an alkali metal hydride such as sodium or potassium hydride, a sodium ($C_1$–$C_4$ alkoxide), a potassium ($C_1$–$C_4$ alkoxide), sodium amide, a tri-[($C_1$–$C_6$)alkyl]amide or an organometallic base such as n-butyllithium, s-butyllithium, t-butyllithium, lithium diisopropylamide, lithium bis (trimethylsilyl)amide, sodium diisopropylamide or sodium bis(trimethylsilyl)amide. The reaction temperature can range from about 0° C. to about 180° C. and is preferably from about 50° C. to about 140° C. Suitable solvents include DMSO, THF, sulfolane, dioxane and NMP.

When Z is CHCN or CHCOO($C_1$–$C_4$ alkyl), a base that is capable of deprotonating $R^5ZH$ may be used, such as an alkali metal hydride (e.g., sodium or potassium hydride), a sodium ($C_1$–$C_4$ alkoxide) or an organometallic base such as n-butyllithium, s-butyllithium, t-butyllithium, lithium diisopropylamide, lithium bis(trimethylsilyl)amide, sodium diisopropylamide or sodium bis(trimethylsilyl)amide, in an appropriate solvent, e.g., THF, DMSO, dioxane, methylene chloride, chloroform, toluene, xylene, benzene or a $C_1$–$C_6$ alkanol.

When Z is $CR^{13}CN$, compounds of formula I may be prepared by reacting the corresponding compounds wherein Z is CHCN first with a base such as an alkali metal hydride such as sodium or potassium hydride, n-butyllithium, s-butyllithium, t-butyllithium, lithium diisopropylamide, lithium bis(trimethylsilyl)amide or sodium diisopropylamide, and then with a compound of the formula $R^{13}L$ wherein L is a leaving group such as iodo, chloro, bromo, mesylate (OMs) or tosylate (OTs).

Compounds of the formula I wherein Z is $CHR^{13}$ may be prepared by acid hydrolysis (using, e.g., 85% phosphoric acid) of the corresponding compounds wherein Z is $CR^{13}CN$, followed by decarboxylation upon heating in an oil bath at a temperature from. about 120° C. to about 180° C. Further alkylation in the presence of base and a compound of the formula and $R^{14}L$, wherein L is defined as above, will provide the corresponding compounds of formula I wherein Z is $CR^{13}R^{14}$.

When Z is N($C_1$–$C_4$ alkyl), compounds of the formula I may be prepared by reacting the corresponding compounds wherein Z is NH first with a base and then with a compound of the formula ($C_1$–$C_4$ alkyl)-L, wherein L is defined as above. Bases such as lithium diisopropylamide, lithium bis(trimethylsilyl)amide, sodium diisopropylamide may be used. Suitable solvents include THF, methylene chloride ($CH_2Cl_2$), DMSO, DMP, NMP and dioxane. The reaction temperature may range from about 20° C. to about 150° C., and is preferably from about room temperature to about 100° C.

Compounds of formula I wherein D is carbon and B is $-NR^1R^2$, $-OCHR^1R^2$ or $-SCHR^1R^2$ may be prepared by reacting the corresponding compounds of formula III, wherein U is chloro, bromo or iodo, with a compound of the formula BH in the presence of a base, using methods analogous to those described above for the conversion of compounds of the formula II into compounds of the formula I.

Compounds of formula I wherein D is carbon and B is $-CR^1R^2R^{10}$, $-C(=CR^2R^{11})R^1$, $-CR^2R^{10}NHR^1$, $-CR^2R^{10}OR^1$, $-CR^2R^{10}SR^1$ or $-COR^2$ may be prepared by reacting the corresponding compounds of formula III, wherein U is cyano, with a Grignard reagent containing the desired $R^2$ group to form a compound of the formula I wherein B is $COR^2$. Further reaction of this compound with a Grignard reagent containing the desired $R^1$ group will yield the compound of formula I wherein B is —$CR^1R^2(OH)$.

Compounds of the formula I wherein B is —$CR^1R^2R^{11}$, or —$C(C=CR^2R^{11})R^1$ may be prepared using conventional methods well known to those skilled in the art. For example, reaction of compounds of the formula I wherein B is —$C(OH)R^1R^2$ with an acid such as concentrated sulfuric acid in acetic acid, or a Burgess inner salt (such as (carboxysulfamoyl)triethylammonium hydroxide methyl ester) will yield a compound of the formula I wherein B is —$C(=CR^2R^{11})R^1$. Hydrogenation of a compound of the formula I wherein B is —$C(=CR^2R^{11})R^1$ using a Pd/C (palladium on carbon) or platinum oxide catalyst, using standard methods well known in the art, will yield a compound of formula I wherein B is —$CHR^1R^2$. Reaction of compounds in formula I wherein B is —$CR^1R^2(OH)$ with diethylaminosulfur trifluoride or triphenylphosphine/carbon tetrachloride will afford a compound of formula I wherein B is —$CR^1R^2F$ or —$CR^1R^2Cl$, respectively.

Reduction of compounds of the formula I wherein B is —$COR^2$ with sodium borohydride in a reaction inert solvent such as a ($C_1$–$C_4$ alcohol), THF or dioxane, preferably methanol, at a temperature from about room temperature to about 100° C, preferably from about room temperature to about 60° C., will yield a compound of the formula I wherein B is —$CHR^2OH$. Alkylation of the —$CHR^2OH$ group with an alkyl halide (such as an alkyl iodide) in the presence of a base (such as sodium hydride, potassium hydride or sodium or lithium bis(trimethylsilyl)amide) at about room temperature will afford the corresponding compound of formula I wherein B is —$CHR^2OR^1$. Compounds of formula I wherein B is —$CR^2R^{10}NHR^1$ may also be prepared by a conventional methods well known in the art, such as reductive amination of the corresponding compounds of formula I wherein B is —$COR^2$ with an appropriate amine and reducing agent (e.g., sodium cyanoborohydride or sodium triacetoxylborohydride) in an appropriate solvent (e.g., a lower alkanol or acetic acid).

Compounds of the formula ill wherein U is CN may be prepared by reacting the corresponding compounds of the formula III wherein U is chloro, bromo, iodo, or —$OCOCF_3$ with potassium cyanide or copper cyanide in dimethylsulfoxide, THF, methylene chloride, toluene or DMF, with or without a Pd(0) or Pd(II) catalyst, at a temperature from about room temperature to about 180° C., preferably at about the reflux temperature.

Compounds of the formula Ill wherein U is chloro, bromo, iodo, or —$OCOCF_3$ may be prepared from the corresponding compounds of the formula III wherein U is hydroxy or amino. Compounds of the formula III wherein U is halo, or —$OCOCF_3$ may be prepared by reacting a compound of the formula III wherein U is amino with a compound of the formula ($C_1$–$C_5$ alkyl)-O-N=O and a copper (II) halide in an appropriate solvent such as acetonitrile, acetone, toluene, methylene chloride or dichloroethane, at a temperature from about room temperature to about the reflux temperature. This reaction is preferably carried out in acetonitrile at the reflux temperature.

Compounds of formula III wherein U is chloro or bromo may be prepared by reacting the corresponding compounds of the formula III wherein U is hydroxy with a compound of the formula $POX_3$, wherein X is chloro or bromo, with or without di-($C_1$–$C_4$alkyl)aniline. This reaction may be conducted neat or in a solvent such as dimethylformamide, dichloroethane or methylene chloride, at a temperature from about 100° C. to about 180° C. Compounds of formula III wherein U is —OTf (wherein Tf is triflate) may be prepared by reacting the corresponding compounds of the formula III wherein U is OH with $Tf_2O$ in the presence of a base such as tri-($C_1$–$C_4$ alkyl) amine or pyridine or an appropriate pyridine derivative (e.g., dimethylaminopyridine) in an appropriate solvent such as methylene chloride, DMF, DMSO, chloroform, or THF. Reaction of compounds of formula III wherein U is OTf with a compound of the formula KX, NaX or CuX (wherein X is chloro, bromo or iodo) in an appropriate solvent such as DMF, dimethylacetamide, N-methyl-pyrrolidone (NMP), or DMSO at temperature between about room temperature and about 180° C. will yield compounds of the formula III wherein U is chloro, bromo or iodo.

Compounds of formula I, II, and III, wherein Z and $R^5$ are defined as above for formula I and $R^3$ is —$O$-($C_1$–$C_4$) alkyl or —$S$-($C_1$–$C_4$) alkyl (hereinafter $R^{20}$) may be prepared by reacting the corresponding compounds of the formula I, wherein $R^3$ is chloro, bromo, OTs or iodo, with a nucleophile of the formula $R^{20}H$, wherein $R^{20}H$ is a ($C_1$–$C_6$) alkanol or a ($C_1$–$C_6$)alkane thiol, optionally in the presence of an organic or inorganic base. Suitable bases include sodium, sodium hydride, potassium hydride, lithium diisopropylamide, lithium bis(trimethylsilyl)amide and sodium diisopropylamide. Compounds of the formula I wherein $R^3$ is fluoro may be prepared by reacting the corresponding compounds wherein $R^3$ is chloro, bromo, iodo, —$OCOCF_3$, or —$OSO_2CF_3$ with tetrabutylammonium fluoride, potassium fluoride or another suitable fluoride agent, using standard methods well known to those skilled in the art.

Compounds of formula I wherein G is O, S, or $NR^8$ may be prepared from compounds of formula IV-a, as illustrated in Scheme 1. Referring to Scheme 1, compounds of the formula IV-b may be prepared by reacting the appropriate compound of the formula IV-a, wherein B is —$CR^1R^2R^{10}$, —$C(=CR^2R^{11})R^1$, $CR^1R^{10}OR^1$, $CR^2R^{10}SR^1$ or $COR2$; Y is O, S, $NR^8$; and A is $CR^7$ or N, with an acyl halide such as L-($CH_2$)$_n$—COX (wherein X is chloro, bromo, iodo, mesylate, tosylate, triflate or $OCOCF_3$; and L is chloro, bromo, iodo, hydroxy, mesylate, tosylate, triflate or $OCOCF_3$), or an anhydride (such as [$C_1$–$C_4$alkyl)CO]$_2$O) in the presence of a base such as a tri-($C_1$–$C_4$ alkyl)amine, pyridine or a substituted pyridine, in an appropriate solvent such as methylene chloride, chloroform, THF, DMSO, dioxane, ether, dimethoxyethane, at a temperature from about 0° C. to about 180° C., preferably from about room temperature and about 60° C.

Compounds of formula Ia may be prepared by reacting the corresponding compounds of the formula IV-b with a base. Suitable bases for use in this reaction include sodium, sodium hydride, potassium hydride, lithium diisopropylamide, butyl lithium, lithium bis(trimethylsilyl) amide, sodium diisopropylamide or sodium or potassium carbonate. Alkylation of the resulting compounds of the formula Ia with a base, followed by quenching with alkyl halide in an appropriate solvent such as ether, THF, methylene chloride, dioxane, benzene, toluene, or dimethoxyethane (DME), with or without hexamethylphosphoramide (HMPA), at temperature from about −78° C. to about room temperature, will afford the corresponding compounds of the formula Ic. Suitable bases for use in this reaction include lithium diisopropyilnide, lithium bis(trimethylsilyl)amide, sodium diisopropylamide, and butyl lithium. Reduction of compounds of the formula I-a or I-c with a reducing agent such as borane methyl sulfide complex ($BH_3$•DMS), borane ($BH_3$), borane THF complex ($BH_3$•DMS), diisobutylaluminum hydride or lithium aluminum hydride will yield the corresponding compounds of the formula I-b or I-d, respectively.

Compounds of formula I wherein G is carbon may be prepared from compounds of formula IV-c, as illustrated in Scheme 2. Referring to scheme 2, compounds of formula 1-e may be prepared by cyclization of compounds of formula IV-c wherein Q is $(C_1-C_2 \text{ alkyl})CR^4(COOC_1-C_4 \text{ alkyl})_2$, $(C_1-C_2 \text{ alkyl})CR^4(COOC_1-C_4 \text{ alky})$, $(C_1-C_2 \text{ alkyl})CR^4(CN)_2$, $(C_1-C_2 \text{ alkyl})CR^4(CN)$ or $(C_1-C_2 \text{ alkyl})CR^4COOH$ using standard methods for amide formation that are well known in the literature. Such methods include acid cyclization (such as: (a) heating in 40–85% phosphoric acid at a temperature from about 100° C. to about 150° C.; (b) heating in aqueous acetic acid/hydrochloric acid; or (c) base hydrolysis; followed by decarboxylation and then amide cyclization). Compounds of formula I-f may be obtained by reduction of the corresponding compounds of the formula I-e using the methods analogous to those described above for conversion of compounds of the formula I-a into those of the formula I-b.

Compounds of formula IV-c wherein Q is $(C_1-C_2 \text{ alkyl})CR^4(COOC_1-C_4 \text{ alkyl})_2$ or $(C_1-C_2 \text{ alkyl})CR^4(CN)_2$ can be prepared by reaction of a compound of the formula Na—, K— or Li—$CR^4(COOC^1-C^4 \text{ alkyl})_2$ or Na—, K— or Li—$CR^4(CN)_2$ with a compound in formula IV-c wherein Q is $CHR^8X$ or $CHR^8CHR^4X$ (wherein X is chloro, bromo or iodo), at a temperature between about 0° C. and about 150° C., preferably between about 10° C. to about 60° C., in an appropriate solvent such as THF, DMSO, DMF, a $(C_1-C_5$ alkyl)-alcohol, acetonitrile, acetone, toluene, NMP or dimethyl acetamide. The preferred solvent is DMSO. Other compounds of formula IV may be prepared by methods analogous to those described in World Patent Application WO 95/33750, which designates the United States and which was published on May 18, 1995. This application is incorporated herein by reference in its entirety.

Compounds of formula I wherein E is $CR^6$, G is $CR^8$, D is nitrogen and K is oxygen may be prepared by reacting compounds of the formula IV-c wherein Q is $CHR^8OH$ with aqueous formaldehyde or $R^6CHO$ in an appropriate solvent such as benzene, toluene, xylene, a $C_1-C_5$ alkyl alcohol or acetonitrile, in the presence of acid catalyst such as p-TsOH, $H_2SO_4$ or HCl, at a temperature from about room temperature to about 160° C., preferably at about the reflux temperature. Toluene or benzene is preferred solvent.

Compounds of formula IV-c may be prepared by the methods described in World Patent Application WO 95/33750, which designates the United States and was published on May 18,1995.

The acid addition salts of compounds of the formula can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The compounds of formula I and their pharmaceutically acceptable salts (hereinafter referred to, collectively, as "the active compounds of this invention") may be administered alone or in combination with pharmaceutically acceptable carriers, in either single or multiple doses. Suitable pharmaceutical carriers include inert solid diluents or fillers, sterile aqueous solutions and various organic solvents The pharmaceutical compositions formed by combining the novel compounds of formula I and pharmaceutically acceptable carriers can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for the active compounds of this invention will depend on the intended route of administration and factors such as the age and weight of the patient, as generally known to a physician. The dosages will also depend on the particular illness to be treated. For instance, the daily dosage for stress-induced illnesses, inflammatory disorders, Alzheimer's disease, gastrointestinal diseases, anorexia nervosa, hemorrhagic stress and drug and alcohol withdrawal symptoms will generally range from about 0.1 to about 50 mg/kg body weight of the patient to be treated.

Methods that may be used to determine the CRF antagonist activity of the active compounds of this invention and their pharmaceutically acceptable salts are described in *Endocrinology*, 116, 1653–1659 (1985) and *Peptides*, 10, 179–188 (1985). The binding activities for compounds of the formula I, expressed as $IC_{50}$ values, generally range from about 0.5 nanomolar to about 10 micromolar. Methods that can be used to determine the CRF binding protein inhibiting activity of compounds of the formula I can be determined using the method described in *Brain Research*, (1997), 745 (1,2), 248–255.

The present invention is illustrated by the following examples. It will be understood, however, that the invention is not limited to the specific details of these examples. Melting points are uncorrected. Proton nuclear magnetic resonance spectra ($^1H$ NMR) and $C^{13}$ nuclear magnetic resonance spectra ($C^{13}$ NMR) were measured for solutions in deuterochloroform ($CDCl_3$) and peak positions are expressed in parts per million (ppm) downfield from tetram-

EXAMPLE 1

1-(1-Ethyl-propyl)-7-methyl-5-(2,4,6-trimethyl-phenoxy)-1,4-dihydro-2H-pyrido[3,4-b]pyrazin-3-one To a solution of 2-chloro-N-[4-(1-ethyl-propylamino)-6-methyl-2-(2,4,6-trimethyl-phenoxy)-pyridin-3-yl]-acetamide (170 mg, 0.42 mml) in 2 ml of dry THF was added a solution of 1 M lithium bis(trimethylsilyl)amide in THF (0.84 ml, 0.84 mmol) at −78° C. The mixture was gradually warmed to room temperature and stirred at room temperature for 2 hours. An additional 0.42 ml of 1M lithium bis(trimethylsilyl)amide in HF was added at −78° C. and the resulting mixture was stirred at room temperature overnight. The mixture was quenched with water and extracted with ethyl acetate. The organic layer was dried and concentrated to dryness to give 160 mg of yellow solid. The solid residue was purified through silica gel column chromatography using 15% ethyl acetate (EtOAc) in hexane as eluent to give 91 mg (59%) of the title compound as white crystals. $^1$H NMR (CDCl$_3$) δ 7.84 (s, 1H), 6.88 (s,2H), 6.22 (s,1H), 3.82(s,2H), 3.58(m,1H), 2.30(s,3H), 2.18(s,3H), 2.08(s,6H), 1.63(m,4H), 0.95(m,6H) ppm.

EXAMPLE 2

1-(1-Ethyl-Propyl)4,7-dimethyl-5-(2,4,6-trimethyl-phenoxy-1,4-Dihydro-2H-pyrido[3,4-b]pyrazin-3-one To a solution of 1-(1-Ethyl-propyl)-7-methyl-5-(2,4,6-trimethyl-phenoxy)-1,4-dihydro-2H-pyrido[3,4-b]pyrazin-3-one (50 mg, 0.136 mmol) in 2 ml of dry THF was added IM lithium bis(trimethylsilyl)amide in THF (0.14 ml) at −78° C. and the mixture was stirred at that temperature for 20 min. An excess of methyl iodide was added at −78° C. and the resulting mixture was stirred at that temperature for 20 min, then gradually warmed to room temperature and stirred for an additional 2 hours. The mixture was quenched with water and extracted with ethyl acetate. The organic layer was dried and concentrated to give 61 mg of pale yellow solid. The solid was purified through silica gel column chromatography using 10% ethyl acetate in hexane as eluent to give 28 mg of the title compound as white crystals, mp 112–114° C.; $^1$H NMR (CDCl$_3$) δ 6.89(s,2H), 6.29(s,1H), 3.63(s,2H), 3.59(s,3H), 3.48(m,1H), 2.31(s,3H), 2.18(s,3H), 2.10(s,6H), 1.60(m,4H), 0.94(t,6H) ppm.

EXAMPLE 3

1-(1-Ethyl-propyl)-4,7-dimethyl-5-(2,4,6-trimethyl-phenoxy)-1,2,3,4-tetrahydro-pyrido[3,4-b]pyrazine A mixture of 1-(1-Ethyl-propyl)-4,7-dimethyl-5-(2,4,6-trimethyl-phenoxy)-1,4-dihydro-2H-pyrido[3,4-b]pyrazin-3-one (21 mg, 0.055 mmol) and 2 M borane dimethylsulfide complex (BH$_3$•DMS) (0.07 ml, 0.14 mmol) in 2 ml of dry THF was heated at reflux for 3 hours. The mixture was cooled to 0° C. and quenched with 0.2 ml of meoh and 0.2 ml of concentrated hydrochloric acid (HCl). The resulting mixture was stirred at room temperature for 2 hours and concentrated to dryness. The residue was quenched with water and extracted with chloroform. The organic layer was dried and concentrated to give 19 mg of a clear oil that was purified through silica gel column chromatography using 10% ethyl acetate in hexane as eluent to give 11 mg of the title compound as white crystals, mp 78–80° C.; $^1$H NMR (CDCl$_3$) δ 6.85(s,2H), 6.28(s,1H), 3.73(m,1H), 3.12 (m,4H), 2.85(s,3H), 2.29(s,3H), 2.,13(s,3H), 2.11 (s,6H), 1.61(m,4H), 0.90(t,6H) ppm.

EXAMPLE 4

1-(1-Ethyl-propyl)-7-methyl-5-(2,4,6-trimethyl-phenoxy)-1,2,3,4-tetrahydro-pyrido[3,4-b]pyrazine The title compound was prepared as a tan crystals, mp 138–140° C., by the procedure analogous to that in Example 3 starting from 1-(1-ethyl-propyl)-7-methyl-5-(2,4,6-trimethyl-phenoxy)-1,4-dihydro-2H-pyrido[3,4b]pyrazin-3-one. $^1$H NMR (CDCl$_3$) δ 6.87(s,2H), 6.17(s,1H), 3.62(m, 1H), 3.39(m,2H), 3.32(m,2H), 2.29(s,3H), 2.13(s,3H), 2.11 (s,6H), 1.59(m,4H), 0.91(t,6H) ppm.

EXAMPLE 5

1-(1-Ethyl-propyl)7-methyl2-oxo5-(2,4,6-trimethyl-phenoxy)-1,2,3,4-tetrahydro-[1,6]naphthyridine-3-carboxylic Acid Methyl Ester A mixture of 2-[4-(1-ethyl-propylamino)-6-methyl-2-(2,4,6-trimethyl-phenoxy)-pyridin-3-ylmethyl]-malonic acid dimethyl ester (22 mg, 0.048 mmol) and 2 ml of acetic acid and bubbled through HCl (g) was heated at 130° C. for 30 hours. The reaction was cooled and concentrated to dryness. The residue was quenched with water and extracted with ethyl acetate. The organic layer was dried and concentrated to give 7 mg of the title compound. $^1$H NMR (CDCl$_3$) δ 6.89(s,2H), 6.59(s,1H), 4.4(m,1H), 3.72(s,3H), 3.6–3.8(m, 1H), 3.4–3.6(m,1H), 3.1–3.2(dd,1 H), 2.31(s,3H), 2.28(s, 3H), 2.06(s,6H), 1.8–2.2(m,4H), 0.92(t,6H) ppm.

EXAMPLE 6

1-(1-Ethyl-propyl)-7-methyl-2-oxo-5-(2,4,6-trimethyl-phenoxy)-1,2,3,4-tetrahydro-[1,6] naphthyridine3-carboxylic Acid Isopropyl Ester The title compound was prepared by the method analogous to that in Example 5 starting from 2-[4-(1-ethyl-propylamino)-6-methyl-2-(2,4,6-trimethyl-phenoxy)-pyridin-3-ylmethyl]-malonic acid diisopropyl ester. $^1$H NMR (CDCl$_3$) δ 6.88(s,2H), 6.57(s,1H), 5.00(m,1H), 3.4–3.6(m,2H), 3.15(dd,1H), 2.30(s,3H), 2.24(s,3H), 2.05(s, 6H), 2.0–2.3(m,3H), 1.75–1.95(m,2H), 1.22(d,3H), 1.14(d, 3H), 0.93(t,6H) ppm.

EXAMPLE 7

1-(1-Ethyl-propyl)-7-methyl-5-(2,4,6-trimethyl-phenoxy)-3,4-dihydro-1H-[1,6]naphthyridin-2-one A mixture of 2-[4-(1-ethyl-propylamino)-6-methyl-2-(2,4,6-trimethyl-phenoxy)-pyridin-3-ylmethyl]-malonic acid diisopropyl ester (40 mg, 0.078 mmol) and 85% phosphoric acid was heated at 73° C. overnight, and then heated at 133° C. for 1 hour. The reaction mixture was cooled, quenched with water and extracted with ethyl acetate. The organic layer was washed with brine, dried and concentrated to give a brown oil. The oil residue was purified through silica gel column chromatography using 3% ethyl acetate in hexane as eluent to give 28 mg (98%) of the title compound. $^1$H NMR (CDCl$_3$) δ 6.89(s,2H), 6.56(s,1H), 4.4(m,1H), 3.00(m,2H), 2.67(m,2H), 2.31(s,3H), 2.25(s,3H), 2.07(s,6H), 1.86(m, 4H), 0.90(t,6H) ppm.

EXAMPLE 8

1-(1-Ethyl-propyl)-7-methyl-5-(2,4,6-trimethyl-phenoxy)-1,2,3,4-tetrahydro-[1,6]naphthyridine The title compound was prepared as a white solid, by the procedure analogous to that of EXAMPLE 3 starting from 1-(1-ethyl-propyl)-7-methyl-5-(2,4,6-trimethyl-phenoxy)-3,4-dihydro-1H-[1,6]naphthyridin-2-one. $^1$H NMR (CDC$_{13}$) δ 6.83(s,2H), 6.14(s,1H), 3.63(m,1H), 3.08(m,2H), 2.75(m, 2H), 2.26(s,3H), 2.10(s,3H), 2.07(s,6H), 1.90(m,2H), 1.54 (m,4H), 0.87(t,6H) ppm.

EXAMPLE 9

1-(1-Ethyl-propyl)-7-methyl-5-(2,4,6-trimethyl-phenoxy)-1,4-dihydro-2H-3-oxa-1,6-diaza-naphthalene A mixture of 1-(1-ethyl-propylamino)-6methyl-2-(2,4,6tnimethyl-phenoxy)-pyridin-3-yl]-methanol (42 mg, 0.122 mmol) and 37% formaldehyde (0.05 ml) and para-toluene-sulfonic acid (p-TsOH) (35 mg) in 3.5 ml of toluene was heated at reflux under a Dean-Stark trap for 15 hours. The mixture was quenched with water, saturated sodium bicarbonate and extracted with ethyl acetate. The oraganic layer was dried and concentrated to give 52 mg of crude product as light green solid. The crude material was purified through silica gel column chromatography using 1:1 hexane/CHCl$_3$ as eluent to give 34 mg (86%) of the title compound as white crystals, mp 112–114° C. $^1$H NMR (CDCl$_3$) δ 6.86(s,2H), 6.25(s,1H), 4.92(s,2H), 4.68(s,2H), 3.54(m,1H), 2.29(s,3H), 2.17(s,3H), 2.07(s,6H), 1.5–1.7(m,4H), 0.95(t,6H) ppm.

EXAMPLE 10

1-(1-Ethyl-propyl)-4,7-dimethyl-5-(2,4,6-trimethyl-phenoxy)-1,4-dihydro-2H-3-oxa-1,6-diaza-naphthalene The title compound was prepared as a white solid by the method analogous to that described in EXAMPLE 9 starting from 1-[4-(1-ethyl-propylamino)-6-methyl-2-(2,4,6-trimethyl-phenoxy)-pyridin-3-yl]-ethanol. $^1$H NMR (CDCl$_3$) δ 6.87(s,2H), 6.26(s,1H), 5.16(q,1H), 4.7(Abq, 2H), 3.63(m,1H), 2.29(s,3H), 2.15(s,3H), 2.08(s,6H), 1.65 (d,3H), 1.5–1.8(m,4H), 0.96(m,6H)ppm.

EXAMPLE 11

1-(1-Ethyl-propyl)-3,7-dimethyl-5-(2,4,6-trimethyl-phenoxy)-3,4-dihydro-1H-[1,6]-naphthyridin-2-one A mixture of 2-[4-(1-ethyl-propylamino)-6-methyl-2-(2,4,6-trimethyl-phenoxy)-pyridin-3-yl]methyl]-2-methyl-malonic acid dimethyl ester (130 mg) and 85% phosphoric acid (4 ml) and water (4 ml) was heated at reflux for 16 hours. The mixture was quenched with water and extracted with ethyl acetate. The organic layer was washed with water and saturated sodium bicarbonate and brine, dried and concentrated to give 80 mg of clear oil. The oil was purified through silica gel column chromatography using hexane to 10% ethyl acetate in hexane as eluent to give 67 mg (64%) of the title compound as a white solid. $^1$H NMR (CDCl$_3$) δ 6.87(s,2H), 6.53(s,1H), 4.3(m,1H), 3.14(m,1H), 2.69(m, 2H), 2.29(s,3H), 2.22(s,3H), 2.05(s,6H), 1.83(m,4H), 1.25 (d,3H), 0.86(t,6H) ppm.

EXAMPLE 12

1-(1-Ethyl-propyl)-3,3,6-trimethyl-4-(2,4,6-trimethyl-phenoxy)-2,3-dihydro-1H-pyrrolo[3,2-c] pyridine A solution of 1-(1-ethyl-propyl)-3,7-dimethyl-5-(2,4,6-trimethyl-phenoxy)-3,4-dihydro-1H-3-oxa-[1,6]-naphthyridin-2-one (56 mg) in 4 ml of dry THF was treated with a 2.0 M borane-dimethyl sulfide complex in THF (0.3 ml) and heated at reflux for 1 hour. The mixture was quenched with water and extracted with ethyl acetate. The organic layer was dried and concentrated to give 50 mg of the title compound as colorless oil. The oil was purified through silica gel column chromatography using 10% ethyl acetate in hexane as eluent to yield 22 mg of the titole compound as white solid, $^1$H NMR (CDCl$_3$) d 6.83(s,2H), 6.15(s,1H), 3.65(m,1H), 3.12(m,1H), 2.98(m,1H), 2.62(m, 1H), 2.26(s,3H), 2.23(m,1H), 2.12(s,3H), 2.06(s,6H), 1.95 (m,1H), 1.57(m,4H), 1.07(d,3H), 0.87(t,6H) ppm.

EXAMPLE 13

[1-(1-Ethyl-propyl)-7-methyl-1,4-dihydro-2H-3-oxa-1,6-diaza-naphthalen-5-yl]-(2,4,6-trimethyl-phenyl)-amine A mixture of [4-(1-ethyl-propylamino)-6-methyl-2-(2,4,6-trimethyl-phenylamino)-pyridin-3-yl]-methanol(280 mg, 0.82 mmol), 37% aqueous formaldehyde(0.35 ml) and p-TsOH (78 mg, 0.41 mmol) in 10 ml of toluene was heated at reflux using a Dean-Stark apparatus for 3 hours. The mixture was quenched with water and extracted with ethyl acetate. The organic layer was separated, dried and concentrated to give 280 mg of a green oil. The oil was purified through silica gel column chromatography using EtOAc as eluent to give the title compound as a brown oil. $^1$H NMR (CDCl$_3$) δ 6.89 (s,2H), 6.09(s,IH), 4.51(s,2H), 4.19(s,2H), 3.53(m,1H), 2.25(s,6H), 2.15(s,6H), 1.55(m,4H), 0.90(t,6H) ppm.

EXAMPLE 14

1-(1-Ethyl-propyl)-7-methyl-5-(2,4,6-trimethyl-phenylamino)-3,4-dihydro-1H-[1,6]naphthyridin-2-one A mixture of 2-[4-(1-ethyl-propylamino)-6-methyl-2-(2, 4,6-trimethyl-phenylamino)-pyridin-3-ylmethyl]-malonic acid dimethyl ester (100 mg, 0.219 mmol), 85% phosphoric acid (3 ml) and water (3 ml) was heated at reflux for 2 hours. The reaction mixture was cooled to rt, diluted with water and neutralized to pH 6 with dilute NaOH and extracted with ethyl acetate. The organic layer was washed with brine, dried over anhydrous MgSO$_4$, filtered, and concentrated to dryness to give 61 mg of a yellow foam. The oil was purified through silca gel column chromatography using 10% EtOAc in hexane as eluent to give 41 mg of the title compound as a tan solid, mp 44–46° C. $^1$H NMR (CDC$_{13}$) δ 6.87(s,2H), 6.36(s,1H), 5.64(brs,1H), 4.21(m,1H), 2.51(m,2H), 2.37(m, 2H), 2.29(s,3H), 2.27(s,3H), 2.11(s,6H), 2.02(m,2H), 1.76 (m,2H), 0.86(t,6H) ppm.

EXAMPLE 15

1-(1-Ethyl-propyl)-7-methyl-5-(2,4,6-trimethyl-phenoxy)-3,4dihydro-1H-pyrido[4,3-d]pyrimidin-2-one To a mixture of [3-Aminomethyl-6-methyl-2-(2,4,6-trimethyl-phenoxy)-pyridin-4-yl]-(1-ethyl-propyl)-amine (100 mg, 0.292 mmol) in dry THF was added triphosgene (34 mg, 0.114 mmol) at 0° C. The reaction mixture was allowed to gradually warm to rt and stir for 2 h. The mixture was quenched with water and extracted with ethyl acetate. The organic layer was dried and concentrated to dryness to give 130 mg of a clear oil. The solid was purified through silica gel column chromatography using 10% EtOAc in hexane as eluent to give 89 mg (82.4%)of the title compound as a white crystalline solid, mp 197–199° C. $^1$H NMR (CDCl$_3$) d 6.86(s,2H), 6.44(s,1H), 5.14(brs,1H), 4.49(s,2H), 4.20(m,1H), 2.28(s,3H), 2.22(s,3H), 2.04(s,6H), 1.67(m, 4H), 0.94(t,6H)ppm.

PREPARATION A

2-Chloro-N-[4-(1-ethyl-propylamino)-6-methyl-2-(2,4,6-trimethyl-phenoxy)-pyridin-3-yl]-acetamide A mixture of 2-(2,4,6-trimethyl-phenoxy)-N4-(1-ethyl-propyl)-6-methyl-pyridine-3,4-diamine (250 mg, 0.76 mmol) and triethylamine (0.11 ml, 0.76 mmol) in 5 ml of dry THF was treated with chloroacetyl chloride (0.06 ml, 0.76 mmol) at 0° C. The resulting mixture was stirred at room temperature for 1 hour. The mixture was quenched with water and extracted with ethyl acetate. The organic layer was dried and concentrated to give 310 mg of green crystals that was purified through silica gel column chromatography using 10% ethyl acetate in hexane as eluent to give 280 mg (90%) of the title compound as tan crystals, mp 152–154° C. $^1$H NMR (CDCl$_3$) δ 8.07(s,1H), 6.88(s,2H), 6.16(s,1H), 4.75(brs,1H), 4.25(s,2H), 3.33(m,1H), 2.30(s,3H), 2.18(s, 3H), 2.08(s,6H), 1,4–1.8(m,4H), 0.97(t,6H) ppm.

PREPARATION B

2-[4-(1-ethyl-propylamino)-6-methyl-2-(2,4,6-trimethyl-phenoxy)-pyridin-3-yl]methyl-2-methyl-malonic Acid Dimethyl Ester A mixture of methyl dimethylmalonate (260 mg) and 60% sodium hydride in oil (70 mg) in 4 ml of DMSO was stirred at room temperature for 10 min. A solution of 3-chloromethyl-6-methyl-2-(2,4,6-trimethyl-phenoxy)-pyridin-4-yl]-(1-ethyl-propyl)-amine (200 mg) in 2 ml of DMSO was added. The mixture was stirred at room temperature for 3 hours. The mixture was quenched with water and extracted with ethyl acetate. The organic layer was dried and concentrated to give the crude material which was purified through silica gel using hexane to 10% ethyl acetate in hexane as eluent to give 137 mg of 2-[4-(1-ethyl-propylamino)-6-methyl-2-(2,4,6-trimethyl-phenoxy)-pyridin-3-yl]methyl]-2-methyl-malonic acid dimethyl ester as a white solid. $^1$H NMR (CDCl$_3$) δ 6.83(s,2H), 6.01(s,1H), 5.00(m,1H), 3.70(s,6H), 3.40(s,2H), 3.25(m,1H), 2.27(s, 3H), 2.12(s,3H), 2.05(s,6H), 1.5–1.7(m,4H), 1.48(s,3H), 0.94(t,6H)ppm.

What is claimed is:
1. A compound of the formula

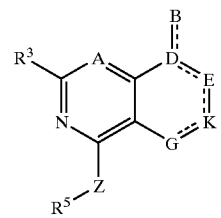

the dashed lines represent optional double bonds;

A is $CR^7$;

B is $-NR^1R^2$, $-CR^1R^2R^{10}$, $-C(=CR^2R^{11})R^1$, $-NHCR^1R^2R^{10}$, $-OCR^1R^2R^{10}$, $-SCR^1R^2R^{10}$, $-CR^2R^{10}NHR^1$, $-CR^2R^{10}OR^1$, $-CR^2R^{10}SR^1$ or $-COR^2$, and is single bonded to D; or B is $-CR^1R^2$, and is double bonded to D and D is carbon;

D is nitrogen or $CR^4$ and is single bonded to all atoms to which it is attached, or D is carbon and is double bonded to E or double bonded to B;

E is nitrogen, C=O, C=S, $CR^6R^{12}$, $NR^6$ or $CR^6$;

K and G are each, independently, C=O, C=S, $CHR^8$ or $NR^8$ when single bonded to both adjacent ring atoms, or nitrogen or $CR^8$ when it is double bonded to an adjacent ring atom;

the 6-membered ring that contains D, E, K and G may contain from one to three double bonds;

with the proviso that one of D, E, K, and G comprises a nitrogen atom that is a member of the 6-membered ring containing D,E, K and G, and the remaining of D, E, K, and G comprise carbon atoms that are each members of said 6-membered ring;

$R^1$ is $C_1$–$C_6$ alkyl optionally substituted with from one or two substituents independently selected from hydroxy, fluoro, chloro, bromo, iodo, $C_1$–$C_4$ alkoxy, $CF_3$, $-C(=O)(C-C_4\text{alkyl})$, $-C(=O)-O-(C_1-C_4)$alkyl, $-OC(=O)(C_1-C_4$ alkyl), $-OC(=O)N(C_1-C_4$ alkyl)($C_1-C_2$ alkyl), $-NHCO(C_1-C_4$ alkyl), $-COOH$, $-COO(C_1-C_4$ alkyl), $-CONH(C_1-C_4$ alkyl), $-CON(C_1-C_4$ alkyl)($C_1-C_2$ alkyl), $-S(C_1-C_4$ alkyl), $-CN$, $-NO_2$, $-SO(C_1-C_4$ alkyl), $-SO_2(C_1-C_4$ alkyl), $-SO_2NH(C_1-C_4$ alkyl) and $-SO_2N(C_1-C_4$ alkyl)($C_1-C_2$ alkyl), wherein each of the $C_1$–$C_4$ alkyl groups in the foregoing $R^1$ groups may optionally contain one or two double or triple bonds;

$R^2$ is $C_1$–$C_{12}$ alkyl which may optionally contain from one to three double or triple bonds, aryl or ($C_1$–$C_4$ alkylene)aryl, wherein said aryl and the aryl moiety of said ($C_1$–$C_4$ alkylene)aryl is selected from phenyl, naphthyl, thienyl, benzothienyl, pyridyl, quinolyl, pyrazinyl, pyrimidinyl, imidazolyl, furanyl, benzofuranyl, benzothiazolyl, isothiazolyl, pyrazolyl, pyrrolyl, indolyl, pyrrolopyridyl, oxazolyl and benzoxazolyl; $C_3$–$C_8$ cycloalkyl or ($C_1$–$C_6$ alkylene)($C_3$–$C_8$ cycloalkyl), wherein one or two of the carbon atoms of said cycloalkyl and the 5 to 8 membered cycloalkyl moieties of said ($C_1$–$C_6$ alkylene)($C_3$–$C_8$ cycloalkyl may optionally and independently be replaced by an oxygen or sulfur and wherein each of the foregoing $R^2$ groups may optionally be substituted with from one to three substituents independently selected from chloro, fluoro, hydroxy and $C_1$–$C_4$ alkyl, or with one substituent selected from $C_1$–$C_6$ alkoxy, —OC(=O)($C_1$–$C_6$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)—CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl); —NR$^1$R$^2$ or CR$^1$R$^2$R$^{10}$ may form a ring selected from saturated 3 to 8 membered rings, the 5 to 8 membered rings of which may optionally contain one or two double bonds, and wherein one or two of the ring carbon atoms of such 5 to 8 membered rings may optionally and independently be replaced by an oxygen or sulfur atom or by NZ$^3$ wherein Z$^3$ is hydrogen or $C_1$–$C_4$ alkyl;

R$^3$ is hydrogen, $C_1$–$C_4$ alkyl, —O($C_1$–$C_4$ alkyl), chloro, fluoro, bromo, iodo, —S($C_1$–$C_4$ alkyl) or —SO$_2$($C_1$–$C_4$ alkyl);

R$^4$ is hydrogen, $C_1$–$C_2$ alkyl, hydroxy or fluoro;

each R$^6$, R$^8$ and R$^9$ that is attached to a carbon atom is selected, independently, from hydrogen, $C_1$–$C_2$ alkyl, fluoro, chloro, bromo, iodo, hydroxy, hydroxymethyl, formyl, trifluoromethyl, cyano, amino, nitro, —O($C_1$–$C_2$ alkyl), —N($C_1$–$C_2$ alkyl)($C_1$–$C_2$ alkyl), —S($C_1$–$C_2$ alkyl), —CO($C_1$–$C_2$ alkyl), —C(=O)H or —C(=O)O($C_1$–$C_2$ alkyl), wherein each of the $C_1$–$C_2$ alkyl moieties in the foregoing R$^6$, R$^8$, and R$^9$ groups may optionally contain one double or triple bond; and each R$^6$, R$^8$, and R$^9$ that is attached to a nitrogen atom is selected, independently, from hydrogen and $C_1$–$C_4$ alkyl;

R$^5$ is substituted phenyl, naphthyl, pyridyl or pyrimidyl, wherein each of the foregoing R$^5$ groups is substituted with from two to four substituents R$^{15}$, wherein from one to three of said substituents may be selected, independently, from chloro, $C_1$–$C_6$ alkyl, —O($C_1$–$C_6$ alkyl) and —($C_1$–$C_6$alkylene)O($C_1$–$C_6$alkyl), and wherein one of said substituents may be selected, independently, from bromo, iodo, formyl, cyano, trifluoromethyl, nitro, amino, —NH($C_1$–$C_4$ alkyl), —N($C_1$–$C_2$ alkyl)($C_1$–$C_6$ alkyl), —C(=O)O($C_1$–$C_4$ alkyl), —C(=O)($C_1$–$C_4$ alkyl), —COOH, —SO$_2$NH($C_1$–$C_4$ alkyl), —SO$_2$N($C_1$–$C_2$ alkyl)($C_1$–$C_4$ alkyl), —SO$_2$NH$_2$, —NHSO$_2$($C_1$–$C_4$ alkyl), —S($C_1$–$C_6$ alkyl) and —SO$_2$($C_1$–$C_6$ alkyl), and wherein each of the $C_1$–$C_4$ alkyl and $C_1$–$C_6$ alkyl moieties in the foregoing R$^5$ groups may optionally be substituted with one or two substituents independently selected from fluoro, hydroxy, amino, methylamino, dimethylamino and acetyl;

R$^7$ is hydrogen, methyl, halo (e.g., chloro, fluoro, iodo or bromo), hydroxy, methoxy, —C(=O)($C_1$–$C_2$ alkyl), —C(=O)O($C_1$–$C_2$ alkyl), trifluoromethoxy, hydroxymethyl, trifluoromethyl or formyl;

R$^{10}$ is hydrogen, hydroxy, methoxy or fluoro; R$^{11}$ is hydrogen or $C_1$–$C_4$ alkyl;

R$^{12}$ is, hydrogen or methyl; and

Z is NH, oxygen, sulfur, —N($C_1$–$C_4$ alkyl), or CR$^{13}$R$^{14}$ wherein R$^{13}$ and R$^{14}$ are independently selected from hydrogen, and methyl with the exception that one of R$^{13}$ and R$^{14}$ may optionally be cyano;

with the further proviso that: (a) in the six or seven membered rings of structures in formula I, there can not be two double bonds adjacent to each other; and (b) when D is carbon and is double bonded to B, then B is CR$^1$R$^2$;

or a pharmaceutically acceptable salt thereof.

2. A compound according to claim 1 wherein B is —CHR$^1$R$^2$ or —NR$^1$R$^2$, and R$^1$ is $C_1$–$C_6$ alkyl which may optionally be substituted with one hydroxy, fluoro, trifluoromethyl or $C_1$–$C_4$ alkoxy group and may optionally contain one double or triple bond; and R$^2$ is benzyl or $C_1$–$C_6$ alkyl which may optionally contain one double or triple bond, and wherein said $C_1$–$C_6$ alkyl and the phenyl moiety of said benzyl may optionally be substituted with one fluoro, $C_1$–$C_2$ alkyl, $C_1$–$C_2$ alkoxy or chloro group.

3. A compound according to claim 1 wherein R$^3$ is methyl, ethyl, chloro or methoxy; R$^6$ R$^8$ and R$^9$ are selected, independently, from hydrogen and methyl; R$^5$ is di- or tri-substituted phenyl, pyridyl, or pyrimidyl, in which up to three of the substitutents can be selected, independently, from $C_1$–$C_4$ alkyl, —O—($C_1$–$C_4$ alkyl) and ($C_1$–$C_2$alkylene)—O—($C_1$–$C_4$ alkyl), and wherein one of the substituents can be selected, independently, from trifluoromethyl, trifluoromethoxy, —CHO, ($C_1$–$C_4$ alkyl)—OH, cyano, chloro, fluoro, bromo, iodo and nitro, and wherein each of the foregoing ($C_1$–$C_4$) alkyl groups may optionally contain one double or triple bond; and Z is oxygen or NH.

4. A compound according to claim 1 wherein A is CH.

5. A compound according to claim 1 that is selected from:

1-(1-ethyl-propyl)-7-methyl-2-oxo-5-(2,4,6-trimethyl-phenoxy)-1,2,3,4-tetrahydro-[1,6]naphthyridine-3-carboxylic acid methyl ester;

1-(1-ethyl-propyl)-7-methyl-2-oxo-5-(2,4,6-trimethyl-phenoxy)-1,2,3,4-tetrahydro-[1,6]naphthyridine-3-carboxylic acid isopropyl ester;

1-(1-ethyl-propyl)-7-methyl-5-(2,4,6-trimethyl-phenoxy)-3,4-dihydro-1H-[1,6]naphthyridin-2-one;

1-(1-ethyl-propyl)-7-methyl-5-(2,4,6-trimethyl-phenoxy)-1,2,3,4-tetrahydro-[1,6]naphthyridine; and 1-(1-ethyl-propyl)-3,7-dimethyl-5-(2,4,6-trimethyl-phenoxy)-3,4-dihydro-1H-[1,6]-naphthyridin-2-one.

6. A compound according to claim 2 wherein B is CHR$^1$R$^2$.

7. A compound according to claim 2 wherein B is NR$^1$R$^2$.

8. A compound according to claim 6 wherein R$^3$ is methyl, ethyl, chloro, or methoxy.

9. A compound according to claim 7 wherein R$^3$ is methyl, ethyl, chloro, or methoxy.

10. A compound according to claim 8 wherein A is CH.

11. A compound according to claim 9 wherein A is CH.

12. A compound according to claim 8 wherein D is N; B—K—G is CR$^6$=CH—C(=O), CR$^6$R$^{12}$—CH$^8$—CHR$^8$, or C(=O)—CR$^8$=CR$^8$.

13. A compound according to claim 12, wherein CR$^6$R$^{12}$ is CH$_2$ and CR$^6$ is CH.

14. A compound according to claim 12, wherein CHR$^8$ is CH$_2$ and CR$^8$ is CH.

15. A compound according to claim 12, wherein CR$^6$R$^{12}$ is CH$_2$, CR$^6$ is CH CHR$^8$ is CH$_2$ and CR$^8$ is CH.

16. A compound according to claim 15, wherein R$^5$ is di- or tri-substituted phenyl, pyridyl, or pyrimidyl, in which the two or three substituents are independently selected from $C_1$–$C_4$ alkyl, O—($C_1$–$C_4$ alkyl), ($C_1$–$C_2$ alkylene)—O—($C_1$–$C_4$ alkyl), trifluoromethyl, trifluoromethoxy, CH(=O), ($C_1$–$C_4$ alkyl)—OH, chloro, fluoro, bromo, iodo, and nitro, and wherein each of the foregoing ($C_1$–$C_4$ alkyl) groups may optionally contain one double or triple bond.

17. A compound according to claim 2 wherein B is NR$^1$R$^2$, or CHR$^1$R$^2$; and the ring containing D, E, K and G is a pyrido ring.

18. A compound according to claim 2, wherein B is $NR^1R^2$, $CHR^1R^2$; and D—E—K—G is C=CH—C(=O)—NH, or C=CH—C(=O)—NMe.

19. A compound according to claim 17, wherein $R^5$ is di- or tri-substituted phenyl, in which the two or three substituents are independently selected from $C_1$–$C_4$ alkyl, O—($C_1$–$C_4$ alkyl), ($C_1$–$C_2$ alkylene)—O—($C_1$–$C_4$ alkyl), trifluoromethyl, trifluoromethoxy, CH(=O), ($C_1$–$C_4$ alkyl)—OH, chloro, fluoro, bromo, iodo, and nitro, and wherein each of the foregoing ($C_1$–$C_4$ alkyl) groups may optionally contain one double or triple bond.

20. A compound according to claim 18, wherein $R^5$ is di- or tri-substituted phenyl, in which the two or three substituents are independently selected from $C_1$–$C_4$ alkyl, O—($C_1$–$C_4$ alkyl), ($C_1$–$C_2$ alkylene)—O—($C_1$–$C_4$ alkyl), trifluoromethyl, trifluoromethoxy, CH(=O), ($C_1$–$C_4$ alkyl)—OH, chloro, fluoro, bromo, iodo, and nitro, and wherein each of the foregoing ($C_1$–$C_4$ alkyl) groups may optionally contain one double or triple bond.

\* \* \* \* \*